US012790333B2

(12) United States Patent
Connolly et al.

(10) Patent No.: US 12,790,333 B2
(45) Date of Patent: Nov. 10, 2026

(54) PIPERIDINYL-METHYL-PURINE AMINE D-TARTARIC ACID SALTS, CRYSTALLINE FORMS, AND THEIR USE IN TREATING MEDICAL DISEASES AND CONDITIONS

(71) Applicant: K36 Therapeutics, Inc., Cambridge, MA (US)

(72) Inventors: Terrence Joseph Connolly, Concord, MA (US); Chad Arthur Lewis, Boylston, MA (US)

(73) Assignee: K36 Therapeutics, Inc., Cambridge, MA (US)

( * ) Notice: Subject to any disclaimer, the term of this patent is extended or adjusted under 35 U.S.C. 154(b) by 734 days.

(21) Appl. No.: 18/198,918

(22) Filed: May 18, 2023

(65) Prior Publication Data

US 2024/0002385 A1 Jan. 4, 2024

Related U.S. Application Data

(60) Provisional application No. 63/343,225, filed on May 18, 2022.

(51) Int. Cl.
*C07D 473/34* (2006.01)

(52) U.S. Cl.
CPC .................................. *C07D 473/34* (2013.01)

(58) Field of Classification Search
CPC .................................................... C07D 473/34
See application file for complete search history.

(56) References Cited

U.S. PATENT DOCUMENTS

| | | | |
|---|---|---|---|
| 11,420,970 | B1 | 8/2022 | Deng et al. |
| 12,312,353 | B2 | 5/2025 | Deng et al. |
| 12,492,203 | B2 | 12/2025 | Connolly et al. |
| 2006/0052403 | A1 | 3/2006 | Isobe et al. |
| 2014/0128389 | A1 | 5/2014 | Halcomb et al. |
| 2014/0161785 | A1 | 6/2014 | Liu et al. |
| 2024/0002385 | A1 | 1/2024 | Connolly et al. |
| 2024/0352017 | A1 | 10/2024 | Connolly et al. |
| 2024/0417401 | A1 | 12/2024 | Connolly et al. |
| 2025/0276971 | A1 | 9/2025 | Deng et al. |
| 2026/0049083 | A1 | 2/2026 | Connolly et al. |

FOREIGN PATENT DOCUMENTS

| | | | |
|---|---|---|---|
| CN | 1512992 | A | 7/2004 |
| CN | 1684966 | A | 10/2005 |
| CN | 1688580 | A | 10/2005 |
| CN | 101679433 | A | 3/2010 |
| CN | 102666541 | A | 9/2012 |
| CN | 108853110 | A | 11/2018 |
| CN | 109223794 | A | 1/2019 |
| CN | 109734677 | A | 5/2019 |
| JP | 2004137157 | A | 5/2004 |
| JP | 2013508373 | A | 3/2013 |
| WO | WO-2000055161 | A1 | 9/2000 |
| WO | WO-2001040217 | A1 | 6/2001 |
| WO | WO-2001040255 | A2 | 6/2001 |
| WO | WO-2002085905 | A1 | 10/2002 |
| WO | WO-2003022216 | A2 | 3/2003 |
| WO | WO-2003022219 | A2 | 3/2003 |
| WO | WO-2003022805 | A2 | 3/2003 |
| WO | WO-2003086404 | A1 | 10/2003 |
| WO | WO-2004029054 | A1 | 4/2004 |
| WO | WO-2004085418 | A2 | 10/2004 |
| WO | WO-2004096130 | A2 | 11/2004 |
| WO | WO-2005123697 | A1 | 12/2005 |
| WO | WO-2006090261 | A1 | 8/2006 |
| WO | WO-2006122137 | A1 | 11/2006 |
| WO | WO-2008114817 | A1 | 9/2008 |
| WO | WO-2008116129 | A2 | 9/2008 |
| WO | WO-2010075074 | A1 | 7/2010 |
| WO | WO-2011049825 | A1 | 4/2011 |
| WO | WO-2011103028 | A2 | 8/2011 |
| WO | WO-2013139882 | A1 | 9/2013 |
| WO | WO-2014121764 | A2 | 8/2014 |
| WO | WO-2015112809 | A2 | 7/2015 |
| WO | WO-2015143424 | A2 | 9/2015 |
| WO | WO-2016073956 | A1 | 5/2016 |
| WO | WO-2017184999 | A1 | 10/2017 |
| WO | WO-2019113469 | A1 | 6/2019 |
| WO | WO-2019196918 | A1 | 10/2019 |
| WO | WO-2020037079 | A1 | 2/2020 |
| WO | WO-2021026803 | A1 | 2/2021 |
| WO | WO-2021028854 | A1 | 2/2021 |
| WO | WO-2023225141 | A1 | 11/2023 |
| WO | WO-2023225144 | A1 | 11/2023 |
| WO | WO-2023225150 | A1 | 11/2023 |
| WO | WO-2023225154 | A1 | 11/2023 |
| WO | WO-2023230026 | A1 | 11/2023 |

OTHER PUBLICATIONS

International Search Report and Written Opinion for International Application No. PCT/CN2019/100542 (13 pages), 2020.
International Search Report and Written Opinion for International Application No. PCT/IB2020/057602 (8 pages), 2020.
Tisi, D. et al., "Structure of the Epigenetic Oncogene MMSET and Inhibition by N-Alkyl Sinefungin Derivatives," *ACS Chem. Bio.*, 2016, vol. 11, No. 11, p. 3093-3105.
Brusova, Chemistry, Moscow State University, (4 pages). Retrieved from the internet on Feb. 10, 2023 from: http://www.chem.msu.su/rus/teaching/brusova/4.html".
Berge, S. M. et al. "Pharmaceutical Salts," *J. Pharmaceutical Sciences*, 1977, vol. 66, No. 1, p. 1-19.
Zhang, L. et al. "Recent advances in nuclear receptor-binding SET domain 2 (NSD2) inhibitors: an update and perspectives," *Eur. J. Med. Chem.*, 2023, 250, 115232.
Caira, M. R. "Crystalline Polymorphism of Organic Compounds." In: *Design of Organic Solids. Topics in Current Chemistry*, ed. E. Weber, Springer, Berlin, 1998, vol. 198, p. 163-208.
International Search Report and Written Opinion for International Application No. PCT/US2023/022643 (8 pages), 2023.
International Search Report and Written Opinion for International Application No. PCT/US2023/022646 (7 pages), 2022.

(Continued)

*Primary Examiner* — Rebecca L Anderson
(74) *Attorney, Agent, or Firm* — Morgan, Lewis & Bockius LLP

(57) ABSTRACT

The invention provides piperidinyl-methyl-purine amine D-tartaric acid salts, crystalline forms, pharmaceutical compositions, their use in inhibiting NSD2, and their use in the treatment of a disease or condition, such as cancer.

28 Claims, 5 Drawing Sheets

(56) References Cited

OTHER PUBLICATIONS

International Search Report and Written Opinion for International Application No. PCT/US2023/022656 (9 pages), 2023.
International Search Report and Written Opinion for International Application No. PCT/US2023/022665 (8 pages), 2023.
Bastin, R. J. et al. "Salt Selection and Optimisation Procedures for Pharmaceutical New Chemical Entities," *Org. Proc. Res. Dev.* 2000, vol. 4, No. 5, p. 427-435.

PIPERIDINYL-METHYL-PURINE AMINE D-TARTARIC ACID SALTS, CRYSTALLINE FORMS, AND THEIR USE IN TREATING MEDICAL DISEASES AND CONDITIONS

CROSS-REFERENCE TO RELATED APPLICATIONS

This application claims the benefit of U.S. Provisional Application No. 63/343,225, filed on May 18, 2022, the entirety of which is hereby incorporated by reference.

FIELD OF THE INVENTION

The invention provides piperidinyl-methyl-purine amine D-tartaric acid salts, crystalline forms, pharmaceutical compositions, their use in inhibiting NSD2, and their use in the treatment of a disease or condition, such as cancer.

BACKGROUND

Cancer continues to be a significant health problem despite the substantial research efforts and scientific advances reported in the literature for treating this disease. Solid tumors, including prostate cancer, breast cancer, and lung cancer remain highly prevalent among the world population. Current treatment options for these cancers are not effective for all patients and/or can have substantial adverse side effects. New therapies are needed to address this unmet need in cancer therapy.

The nuclear receptor-binding SET domain protein 2 (NSD2), also known as multiple myeloma SET domain (MMSET) or Wolf-Hirschhorn syndrome candidate 1 (WHSC1), is an epigenetic modifier having a role in oncogenesis. Several human cancers are associated with NSD2 overexpression and/or activating point mutations. (Coussens et al., *J. Biol. Chem.* 293 (2018) 13750-13654.) For example, high expression of NSD2 has been reported in human cancers including bladder, brain, gastrointestinal, lung, liver, ovary, skin, uterus, breast, prostrate and glioblastoma. Additionally, pediatric cancer genomes appear to be particularly likely to contain NSD2 mutations. Finally, upregulation of NSD2 has been linked with aggressive tumor behavior and poor clinical outcomes. Certain compounds that inhibit NSD2 are described in international patent application publication WO 2021/028854. Additional compounds that inhibit NSD2 would be beneficial to patients suffering from an NSD2-related disease or condition.

The present invention addresses the foregoing needs and provides other related advantages.

SUMMARY

The invention provides piperidinyl-methyl-purine amine D-tartaric acid salts, crystalline forms, pharmaceutical compositions, their use in inhibiting NSD2, and their use in the treatment of a disease or condition, such as cancer. In particular, one aspect of the invention provides a compound that is a D-tartaric acid salt of the following compound:

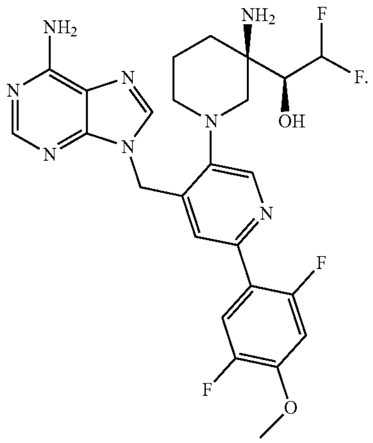 [SMILES: COc1cc(F)c(-c2cc(Cn3cnc4c(N)ncnc43)c(N3CCC[C@](N)([C@H](O)C(F)F)C3)cn2)cc1F]

In certain embodiments, the compound is in crystalline form. One benefit of the D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol is that it has low hygroscopicity. In contrast to the fumaric acid salt, sulfuric acid salt, hydrochloric acid salt, and various other salts of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol that were observed to form hydrates, the D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol could be obtained in anhydrous form and had low hygroscopicity in long-duration stability studies. Another benefit of the D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol is that it displays greater solubility in water than, for example, (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol free base or (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol fumaric acid salt. Yet another benefit of the D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol is that it displayed very good stability to long term storage, showing a high degree of purity after storage in a one year stability study and no detectable loss of crystallinity as measured by XRPD analysis. Further description of additional features of the compounds are described in the detailed description. The compounds may be part of a pharmaceutical composition comprising a pharmaceutically acceptable carrier.

Another aspect of the invention provides a method for treating a disease or condition mediated by nuclear SET domain-containing protein 2 (NSD2). The method comprises administering to a subject in need thereof a therapeutically effective amount of a compound described herein, such as a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol, to treat the disease or condition.

Another aspect of the invention provides a method of inhibiting the activity of nuclear SET domain-containing protein 2 (NSD2). The method comprises contacting a NSD2 with an effective amount of a compound described herein, such as a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol, to inhibit the activity of said NSD2.

DETAILED DESCRIPTION

Figure 1:
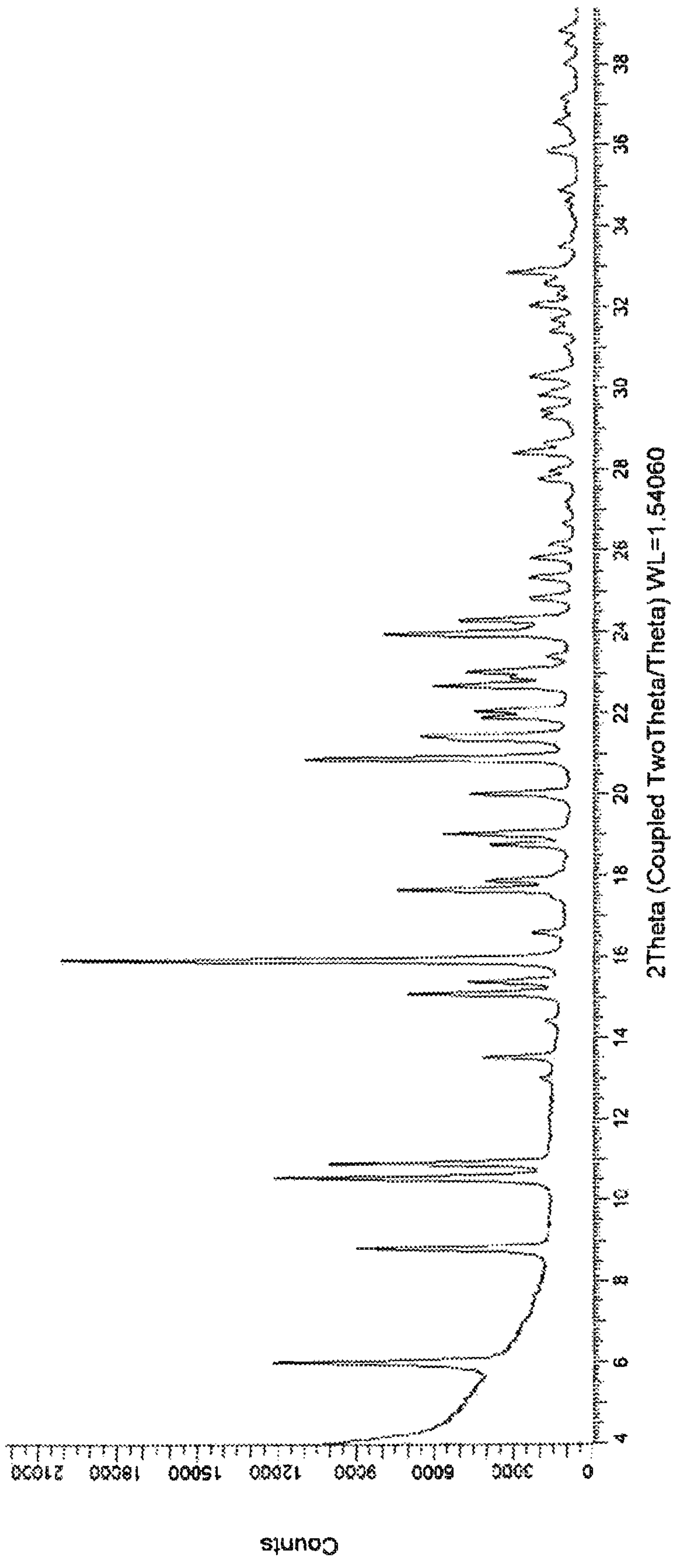
FIG. 1 depicts an X-ray powder diffractogram of one batch of crystalline (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-tartaric acid salt, as further described in Example 4.

The invention provides piperidinyl-methyl-purine amine D-tartaric acid salts, crystalline forms, pharmaceutical compositions, their use in inhibiting NSD2, and their use in the treatment of a disease or condition, such as cancer. One such piperidinyl-methyl-purine amine D-tartaric acid salt is the D-tartaric acid salt of (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol. One benefit of the D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol is that it has low hygroscopicity. In contrast to the fumaric acid salt, sulfuric acid salt, hydrochloric acid salt, and various other salts of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol that were observed to form hydrates, the D-tartaric acid salt of (S)-1-((R)-3-amino-1-(4-((6-amino-9H-purin-9-yl) methyl)-6-(2,5-difluoro-4-methoxyphenyl)pyridin-3-yl)piperidin-3-yl)-2,2-difluoroethan-1-ol could be obtained in anhydrous form and had low hygroscopicity in long-duration stability studies. Another benefit of the D-tartaric acid salt of (S)-1-((R)-3-amino-1-(4-((6-amino-9H-purin-9-yl) methyl)-6-(2,5-difluoro-4-methoxyphenyl)pyridin-3-yl)piperidin-3-yl)-2,2-difluoroethan-1-ol is that it displays greater solubility in water than, for example, (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol free base or (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol fumaric acid salt. Yet another benefit of the D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol is that it displayed very good stability to long term storage, showing a high degree of purity after storage in a one year stability study and no detectable loss of crystallinity as measured by XRPD analysis. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

Compounds of the present invention include those described generally herein, and are further illustrated by the classes, subclasses, and species disclosed herein. As used herein, the following definitions shall apply unless otherwise indicated. These definitions apply regardless of whether a term is used by itself or in combination with other terms, unless otherwise indicated. Hence, the definition of "alkyl" applies to "alkyl" as well as the "alkyl" portions of "—O-alkyl" etc. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "cycloaliphatic"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "—($C_0$ alkylene)-" refers to a bond. Accordingly, the term "—($C_{0-3}$ alkylene)-" encompasses a bond (i.e., $C_0$) and a —($C_{1-3}$ alkylene)-group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, quinolinyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; $—(CH_2)_{0-4}R^{\circ}$; $—(CH_2)_{0-4}OR^{\circ}$; $—O(CH_2)_{0-4}R^{\circ}$, $—O—(CH_2)_{0-4}C(O)OR^{\circ}$; $—(CH_2)_{0-4}CH(OR^{\circ})_2$; $—(CH_2)_{0-4}SR^{\circ}$; $—(CH_2)_{0-4}Ph$, which may be substituted with $R^{\circ}$; $—(CH_2)_{0-4}O(CH_2)_{0-1}Ph$ which may be substituted with $R^{\circ}$; $—CH{=}CHPh$, which may be substituted with $R^{\circ}$; $—(CH_2)_{0-4}O(CH_2)_{0-1}$-pyridyl which may be substituted with $R^{\circ}$; $—NO_2$; —CN; $—N_3$; $—(CH_2)_{0-4}N(R^{\circ})_2$; $—(CH_2)_{0-4}N(R^{\circ})C(O)R^{\circ}$; $—N(R^{\circ})C(S)R^{\circ}$; $—(CH_2)_{0-4}N(R^{\circ})C(O)NR^{\circ}_2$; $—N(R^{\circ})C(S)NR^{\circ}_2$; $—(CH_2)_{0-4}N(R^{\circ})C(O)OR^{\circ}$; $—N(R^{\circ})N(R^{\circ})C(O)R^{\circ}$; $—N(R^{\circ})N(R^{\circ})C(O)NR^{\circ}_2$; $—N(R^{\circ})N(R^{\circ})C(O)OR^{\circ}$; $—(CH_2)_{0-4}C(O)R^{\circ}$; $—C(S)R^{\circ}$; $—(CH_2)_{0-4}C(O)OR^{\circ}$; $—(CH_2)_{0-4}C(O)SR^{\circ}$; $—(CH_2)_{0-4}C(O)OSiR^{\circ}_3$; $—(CH_2)_{0-4}OC(O)R^{\circ}$; $—OC(O)(CH_2)_{0-4}SR—$, $SC(S)SR^{\circ}$; $—(CH_2)_{0-4}SC(O)R^{\circ}$; $—(CH_2)_{0-4}C(O)NR^{\circ}_2$; $—C(S)NR^{\circ}_2$; $—C(S)SR^{\circ}$; $—SC(S)SR^{\circ}$, $—(CH_2)_{0-4}OC(O)NR^{\circ}_2$; $—C(O)N(OR^{\circ})R^{\circ}$; $—C(O)C(O)R^{\circ}$; $—C(O)CH_2C(O)R^{\circ}$; $—C(NOR^{\circ})R^{\circ}$; $—(CH_2)_{0-4}SSR^{\circ}$; $—(CH_2)_{0-4}S(O)_2R^{\circ}$; $—(CH_2)_{0-4}S(O)_2OR^{\circ}$; $—(CH_2)_{0-4}OS(O)_2R^{\circ}$; $—S(O)_2NR^{\circ}_2$; $—S(O)(NR^{\circ})R^{\circ}$; $—S(O)_2N{=}C(NR^{\circ}_2)_2$; $—(CH_2)_{0-4}S(O)R^{\circ}$; $—N(R^{\circ})S(O)_2NR^{\circ}_2$; $—N(R^{\circ})S(O)_2R^{\circ}$; $—N(OR^{\circ})R^{\circ}$; $—C(NH)NR^{\circ}_2$; $—P(O)_2R^{\circ}$; $—P(O)R^{\circ}_2$; $—OP(O)R^{\circ}_2$; $—OP(O)(OR^{\circ})_2$; $SiR^{\circ}_3$; $—(C_{1-4}$ straight or branched alkylene)$O—N(R^{\circ})_2$; or $—(C_{1-4}$ straight or branched alkylene)$C(O)O—N(R^{\circ})_2$.

Each $R^{\circ}$ is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono-or bicyclic ring having 0-4 heteroatoms independently selected from nitrogen, oxygen, or sulfur, which may be substituted by a divalent substituent on a saturated carbon atom of $R^{\circ}$ selected from =O and =S; or each $R^{\circ}$ is optionally substituted with a monovalent substituent independently selected from halogen, $—(CH_2)_{0-2}R^{\bullet}$, -(halo$R^{\bullet}$), $—(CH_2)_{0-2}OH$, $—(CH_2)_{0-2}OR^{\bullet}$, $—(CH_2)_{0-2}CH(OR^{\bullet})_2$; —O(halo$R^{\bullet}$), —CN, $—N_3$, $—(CH_2)_{0-2}C(O)R^{\bullet}$, $—(CH_2)_{0-2}C(O)OH$, $—(CH_2)_{0-2}C(O)OR^{\bullet}$, $—(CH_2)_{0-2}SR^{\bullet}$, $—(CH_2)_{0-2}SH$, $—(CH_2)_{0-2}NH_2$, $—(CH_2)_{0-2}NHR^{\bullet}$, $—(CH_2)_{0-2}NR^{\bullet}_2$, $—NO_2$, $—SiR^{\bullet}_3$, $—OSiR^{\bullet}_3$, $—C(O)SR^{\bullet}$, $—(C_{1-4}$ straight or branched alkylene)$C(O)OR^{\bullet}$, or $—SSR^{\bullet}$.

Each $R^{\bullet}$ is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens; or wherein an optional substituent on a saturated carbon is a divalent substituent independently selected from =O, =S, $=NNR^*_2$, $=NNHC(O)R^*$, $=NNHC(O)OR^*$, $=NNHS(O)_2R^*$, $=NR^*$, $=NOR^*$, $—O(C(R^*_2))_{2-3}O—$, or $—S(C(R^*_2))_{2-3}S—$, or a divalent substituent bound to vicinal substitutable carbons of an "optionally substituted" group is $—O(CR^*_2)_{2-3}O—$, wherein each independent occurrence of $R^*$ is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When $R^*$ is $C_{1-6}$ aliphatic, $R^*$ is optionally substituted with halogen, $—R^{\bullet}$, -(halo$R^{\bullet}$), —OH, $—OR^{\bullet}$, —O(halo$R^{\bullet}$), —CN, —C(O)OH, $—C(O)OR^{\bullet}$, $—NH_2$, $—NHR^{\bullet}$, $—NR^{\bullet}_2$, or $—NO_2$, wherein each $R^{\bullet}$ is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens.

An optional substituent on a substitutable nitrogen is independently $—R^{\dagger}$, $—NR^{\dagger}_2$, $—C(O)R^{\dagger}$, $—C(O)OR^{\dagger}$, $—C(O)C(O)R^{\dagger}$, $—C(O)CH_2C(O)R^{\dagger}$, $—S(O)_2R^{\dagger}$, $—S(O)_2NR^{\dagger}_2$, $—C(S)NR^{\dagger}_2$, $—C(NH)NR^{\dagger}_2$, or $—N(R^{\dagger})S(O)_2R^{\dagger}$; wherein each $R^{\dagger}$ is independently hydrogen, $C_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^\dagger$ is $C_{1-6}$ aliphatic, $R^\dagger$ is optionally substituted with halogen, —$R^\bullet$, -(halo$R^\bullet$), —OH, —$OR^\bullet$, —O(halo$R^\bullet$), —CN, —C(O)OH, —C(O)$OR^\bullet$, —$NH_2$, —$NHR^\bullet$, —$NR^\bullet_2$, or —$NO_2$, wherein each $R^\dagger$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are described in the literature. For example, S. M. Berge et al., describe pharmaceutically acceptable salts in detail in J. Pharmaceutical Sciences, 1977, 66, 1-19, incorporated herein by reference. Pharmaceutically acceptable salts of compounds can include those derived from suitable inorganic and organic acids and bases.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the *IUPAC* 1974 Recommendations. Further, to the extent a compound described herein may exist as a atropisomer (e.g., substituted biaryls), all forms of such atropisomer are considered part of this invention.

Chemical names, common names, and chemical structures may be used interchangeably to describe the same structure. If a chemical compound is referred to using both a chemical structure and a chemical name, and an ambiguity exists between the structure and the name, the structure predominates. It should also be noted that any carbon as well as heteroatom with unsatisfied valences in the text, schemes, examples and tables herein is assumed to have the sufficient number of hydrogen atom(s) to satisfy the valences.

The terms "a" and "an" as used herein mean "one or more" and include the plural unless the context is inappropriate.

Unless specified otherwise, the term "about" refers to within ±10% of the stated value. The invention encompasses embodiments where the value is within ±9%, ±8%, ±7%, ±6%, ±5%, ±4%, ±3%, ±2%, or ±1% of the stated value.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl. The term "cycloalkylene" refers to a bivalent cycloalkyl group.

The term "haloalkyl" refers to an alkyl group that is substituted with at least one halogen. Exemplary haloalkyl groups include —$CH_2F$, —$CHF_2$, —$CF_3$, —$CH_2CF_3$, —$CF_2CF_3$, and the like. The term "haloalkylene" refers to a bivalent haloalkyl group.

The term "hydroxyalkyl" refers to an alkyl group that is substituted with at least one hydroxyl. Exemplary hydroxyalkyl groups include —$CH_2CH_2OH$, —C(H)(OH)$CH_3$, —$CH_2C(H)(OH)CH_2CH_2OH$, and the like.

The terms "alkenyl" and "alkynyl" are art-recognized and refer to unsaturated aliphatic groups analogous in length and possible substitution to the alkyls described above, but that contain at least one double or triple bond respectively.

The terms “alkoxyl” or “alkoxy” are art-recognized and refer to an alkyl group, as defined above, having an oxygen radical attached thereto. Representative alkoxyl groups include methoxy, ethoxy, propyloxy, tert-butoxy and the like. The term “haloalkoxyl” refers to an alkoxyl group that is substituted with at least one halogen. Exemplary haloalkoxyl groups include $—OCH_2F$, $—OCHF_2$, $—OCF_3$, $—OCH_2CF_3$, $—OCF_2CF_3$, and the like.

The term “oxo” is art-recognized and refers to a “=O” substituent. For example, a cyclopentane substituted with an oxo group is cyclopentanone.

The symbol “ $\sim\sim$ ” indicates a point of attachment.

When any substituent or variable occurs more than one time in any constituent or the compound of the invention, its definition on each occurrence is independent of its definition at every other occurrence, unless otherwise indicated.

One or more compounds of the invention may exist in unsolvated as well as solvated forms with pharmaceutically acceptable solvents such as water, and it is intended that the invention embrace both solvated and unsolvated forms. “Solvate” means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. “Solvate” encompasses both solution-phase and isolatable solvates. “Hydrate” is a solvate wherein the solvent molecule is $H_2O$.

As used herein, the terms “subject” and “patient” are used interchangeably and refer to organisms to be treated by the methods of the present invention. Such organisms preferably include, but are not limited to, mammals (e.g., murines, simians, equines, bovines, porcines, canines, felines, and the like), and most preferably includes humans.

The term “$IC_{50}$” is art-recognized and refers to the concentration of a compound that is required to achieve 50% inhibition of the target.

As used herein, the term “effective amount” refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term “treating” includes any effect, e.g., lessening, reducing, modulating, ameliorating or eliminating, that results in the improvement of the condition, disease, disorder, and the like, or ameliorating a symptom thereof.

As used herein, the term “pharmaceutical composition” refers to the combination of an active agent with a carrier, inert or active, making the composition especially suitable for diagnostic or therapeutic use in vivo or ex vivo.

As used herein, the term “pharmaceutically acceptable carrier” refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington’s Pharmaceutical Sciences, 15th Ed., Mack Publ. Co., Easton, PA [1975].

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified.

I. D-Tartaric Acid Salts of (S)-1-((R)-3-Amino-1-(4-((6-amino-9H-purin-9-yl)methyl)-6-(2,5-difluoro-4-methoxyphenyl)pyridin-3-yl)piperidin-3-yl)-2,2-difluoroethan-1-ol The invention provides D-tartaric acid salts of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol. One benefit of the D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol is that it has low hygroscopicity. In contrast to the fumaric acid salt, sulfuric acid salt, hydrochloric acid salt, and various other salts of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol that were observed to form hydrates, the D-tartaric acid salt of (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol could be obtained in anhydrous form and had low hygroscopicity in long-duration stability studies. Another benefit of the D-tartaric acid salt of (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol is that it displays greater solubility in water than, for example, (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol free base or (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol fumaric acid salt. Yet another benefit of the D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol is that it displayed very good stability to long term storage, showing a high degree of purity after storage in a one year stability study and no detectable loss of crystallinity as measured by XRPD analysis. The compounds are described in more detail below. The compounds may be used in the pharmaceutical compositions and therapeutic methods described herein. Exemplary compounds are described in the following sections. Exemplary procedures for making the compounds are described in the Examples.

One aspect of the invention provides a compound that is a D-tartaric acid salt of the following compound:

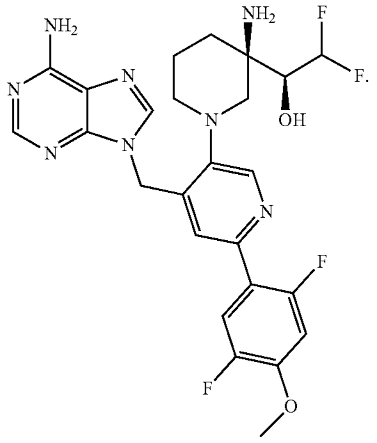 [SMILES: COc1cc(F)c(-c2cc(Cn3cnc4c(N)ncnc43)c(N3CCC[C@](N)([C@H](O)C(F)F)C3)cn2)cc1F]

In certain embodiments, the mole ratio of D-tartaric acid to the following compound is about 1:1:

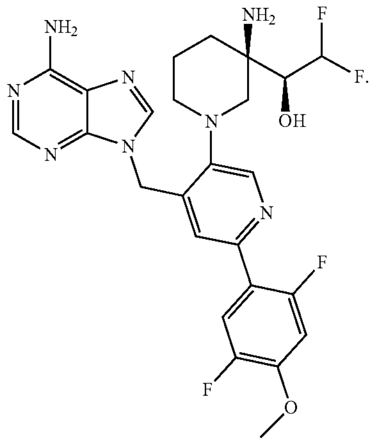 [SMILES: COc1cc(F)c(-c2cc(Cn3cnc4c(N)ncnc43)c(N3CCC[C@](N)([C@H](O)C(F)F)C3)cn2)cc1F]

In certain embodiments, the compound is in crystalline form.

In certain embodiments, the crystalline form exhibits an X-ray powder diffraction pattern comprising peaks at the following diffraction angles (2θ): 6.0±0.2, 8.8±0.2, 10.6±0.2, 10.9±0.2, 15.9±0.2, 20.9±0.2, and 23.9±0.2. In certain embodiments, the X-ray powder diffraction pattern further comprises a peak at the following diffraction angle (2θ): 15.1±0.2. In certain embodiments, the X-ray powder diffraction pattern further comprises a peak at the following diffraction angle (2θ): 17.7±0.2. In certain embodiments, the X-ray powder diffraction pattern further comprises a peak at the following diffraction angle (2θ): 19.0±0.2. In certain embodiments, the X-ray powder diffraction pattern further comprises a peak at the following diffraction angle (2θ): 21.4±0.2. In certain embodiments, the X-ray powder diffraction pattern further comprises a peak at the following diffraction angle (2θ): 22.7±0.2. In certain embodiments, the X-ray powder diffraction pattern further comprises a peak at the following diffraction angle (2θ): 24.3±0.2.

In certain embodiments, the relative intensity of the peak at said diffraction angles (2θ) is at least 30%. In certain embodiments, the relative intensity of the peak at said diffraction angles (2θ) is at least 25%. In certain embodiments, the relative intensity of the peak at said diffraction angles (2θ) is at least 20%. In certain embodiments, the relative intensity of the peak at said diffraction angles (2θ) is at least 15%. In certain embodiments, the relative intensity of the peak at said diffraction angles (2θ) is at least 10%.

In certain embodiments, the crystalline form is characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
|---|---|---|
| 6.0 | 14.7 | 40 |
| 8.8 | 10.0 | 36 |
| 10.6 | 8.4 | 53 |
| 10.9 | 8.1 | 44 |
| 13.5 | 6.5 | 15 |
| 15.1 | 5.9 | 31 |
| 15.4 | 5.8 | 18 |
| 15.9 | 5.6 | 100 |
| 16.6 | 5.3 | 6 |
| 17.7 | 5.0 | 35 |
| 17.9 | 5.0 | 16 |
| 18.8 | 4.7 | 16 |
| 19.0 | 4.7 | 26 |
| 20.0 | 4.4 | 22 |
| 20.9 | 4.3 | 57 |
| 21.4 | 4.1 | 30 |
| 21.9 | 4.1 | 18 |
| 22.0 | 4.0 | 21 |
| 22.7 | 3.9 | 29 |
| 22.9 | 3.9 | 12 |
| 23.0 | 3.9 | 22 |
| 23.4 | 3.8 | 5 |
| 23.9 | 3.7 | 41 |
| 24.3 | 3.7 | 25 |
| 24.8 | 3.6 | 8 |
| 25.3 | 3.5 | 9 |
| 25.8 | 3.4 | 9 |
| 26.2 | 3.4 | 5 |
| 27.8 | 3.2 | 7 |
| 28.0 | 3.2 | 6 |
| 28.4 | 3.1 | 14 |
| 28.6 | 3.1 | 7 |
| 29.5 | 3.0 | 7 |
| 30.3 | 2.9 | 9 |
| 31.4 | 2.8 | 6 |
| 31.7 | 2.8 | 5 |
| 32.0 | 2.8 | 10 |
| 32.6 | 2.7 | 5 |
| 32.9 | 2.7 | 16 |
| 34.9 | 2.6 | 5 |
| 35.8 | 2.5 | 7 |
| 38.8 | 2.3 | 5. |

In certain embodiments, the crystalline form is characterized as having an X-ray powder diffraction pattern substantially as shown in FIG. 1.

In certain embodiments, the crystalline form is characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
|---|---|---|
| 6.0 | 14.7 | 72 |
| 8.4 | 10.5 | 6 |
| 8.8 | 10.0 | 32 |
| 10.6 | 8.4 | 58 |
| 10.9 | 8.1 | 88 |
| 12.9 | 6.9 | 6 |

-continued

| Angle [2θ] | d-spacing [Å] | Relative Intensity [%] |
|---|---|---|
| 13.5 | 6.5 | 24 |
| 14.6 | 6.1 | 6 |
| 15.1 | 5.9 | 31 |
| 15.4 | 5.8 | 24 |
| 15.9 | 5.6 | 100 |
| 16.6 | 5.3 | 5 |
| 17.7 | 5.0 | 28 |
| 17.9 | 5.0 | 26 |
| 18.8 | 4.7 | 22 |
| 19.0 | 4.7 | 36 |
| 20.0 | 4.4 | 40 |
| 20.9 | 4.2 | 82 |
| 21.4 | 4.1 | 37 |
| 21.9 | 4.1 | 29 |
| 22.7 | 3.9 | 35 |
| 23.0 | 3.9 | 35 |
| 23.4 | 3.8 | 10 |
| 24.0 | 3.7 | 49 |
| 24.2 | 3.7 | 29 |
| 24.8 | 3.6 | 10 |
| 25.3 | 3.5 | 13 |
| 25.8 | 3.4 | 9 |
| 26.1 | 3.4 | 7 |
| 27.8 | 3.2 | 7 |
| 28.5 | 3.1 | 8 |
| 29.3 | 3.0 | 6 |
| 29.9 | 3.0 | 9 |
| 30.3 | 2.9 | 9 |
| 31.5 | 2.8 | 5 |
| 32.1 | 2.8 | 9 |
| 32.9 | 2.7 | 9 |
| 35.9 | 2.5 | 5 |
| 36.6 | 2.4 | 6. |

Figure 2:
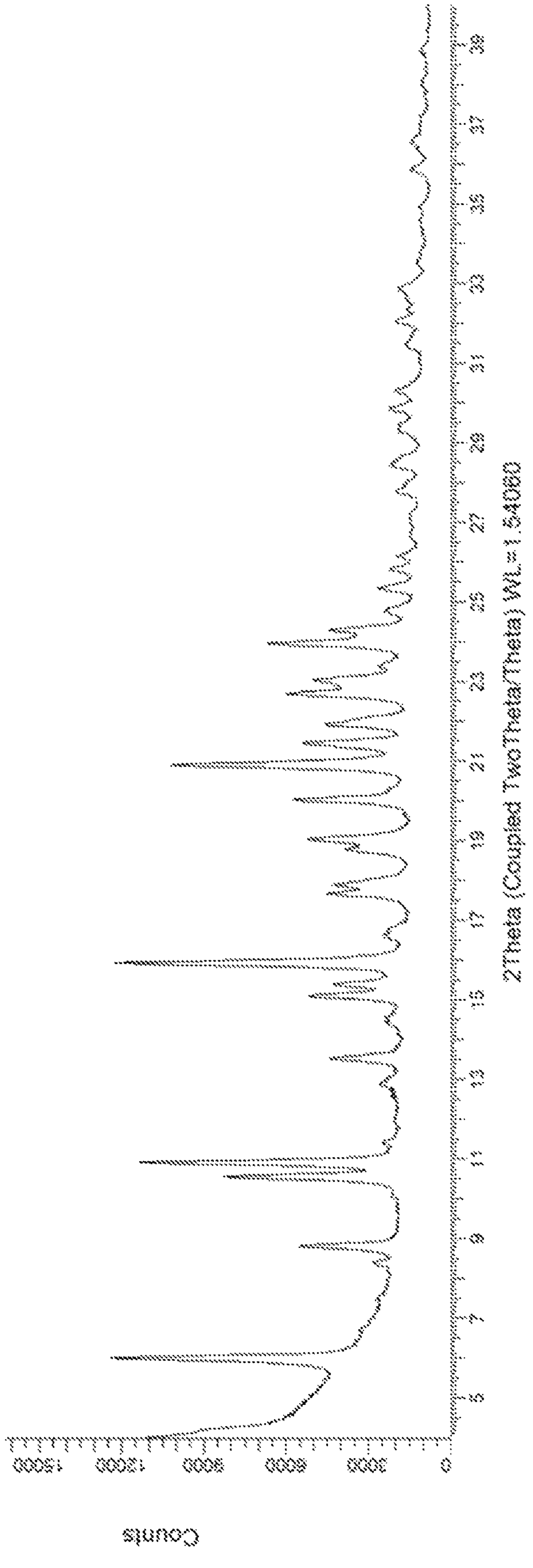
FIG. 2 depicts an X-ray powder diffractogram of a second batch of crystalline (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-tartaric acid salt, as further described in Example 4.

In certain embodiments, the crystalline form is characterized as having an X-ray powder diffraction pattern substantially as shown in FIG. 2.

An X-ray powder diffraction pattern may be obtained using CuKα radiation. The temperature at which the X-ray powder diffraction pattern is obtained may be, for example, 25±2 degrees Celsius.

Figure 4:
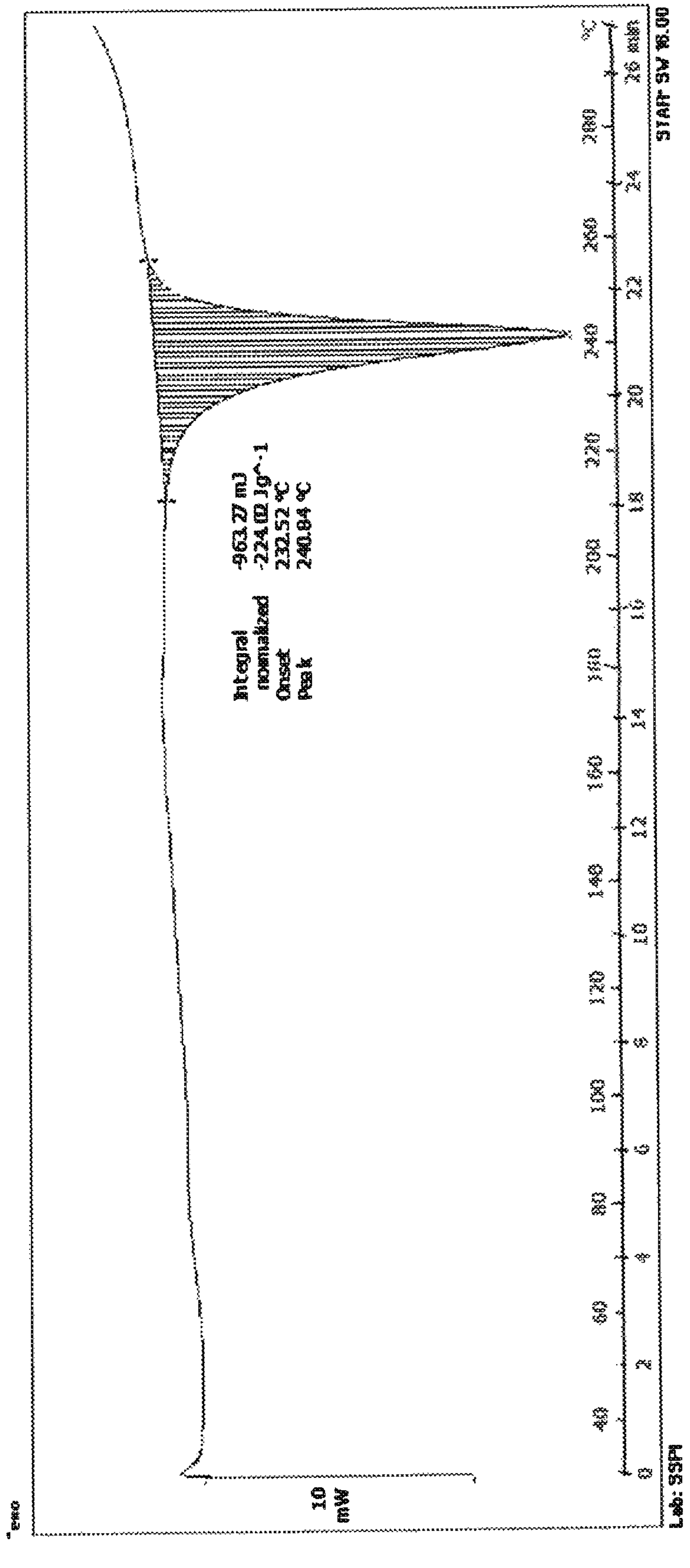
FIG. 4 depicts a differential scanning calorimetry curve of crystalline (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-tartaric acid salt, as further described in Example 4.

In certain embodiments, the compound has a melting point onset as determined by differential scanning calorimetry in the range of from about 225 degrees Celsius to about 240 degrees Celsius. In certain embodiments, the compound has a melting point onset as determined by differential scanning calorimetry at about 233 degrees Celsius. In certain embodiments, the compound has a melting point peak as determined by differential scanning calorimetry in the range of from about 235 degrees Celsius to about 250 degrees Celsius. In certain embodiments, the compound has a melting point peak as determined by differential scanning calorimetry at about 241 degrees Celsius. In certain embodiments, the compound has a differential scanning calorimetry curve substantially the same as shown in FIG. 4.

Figure 5:
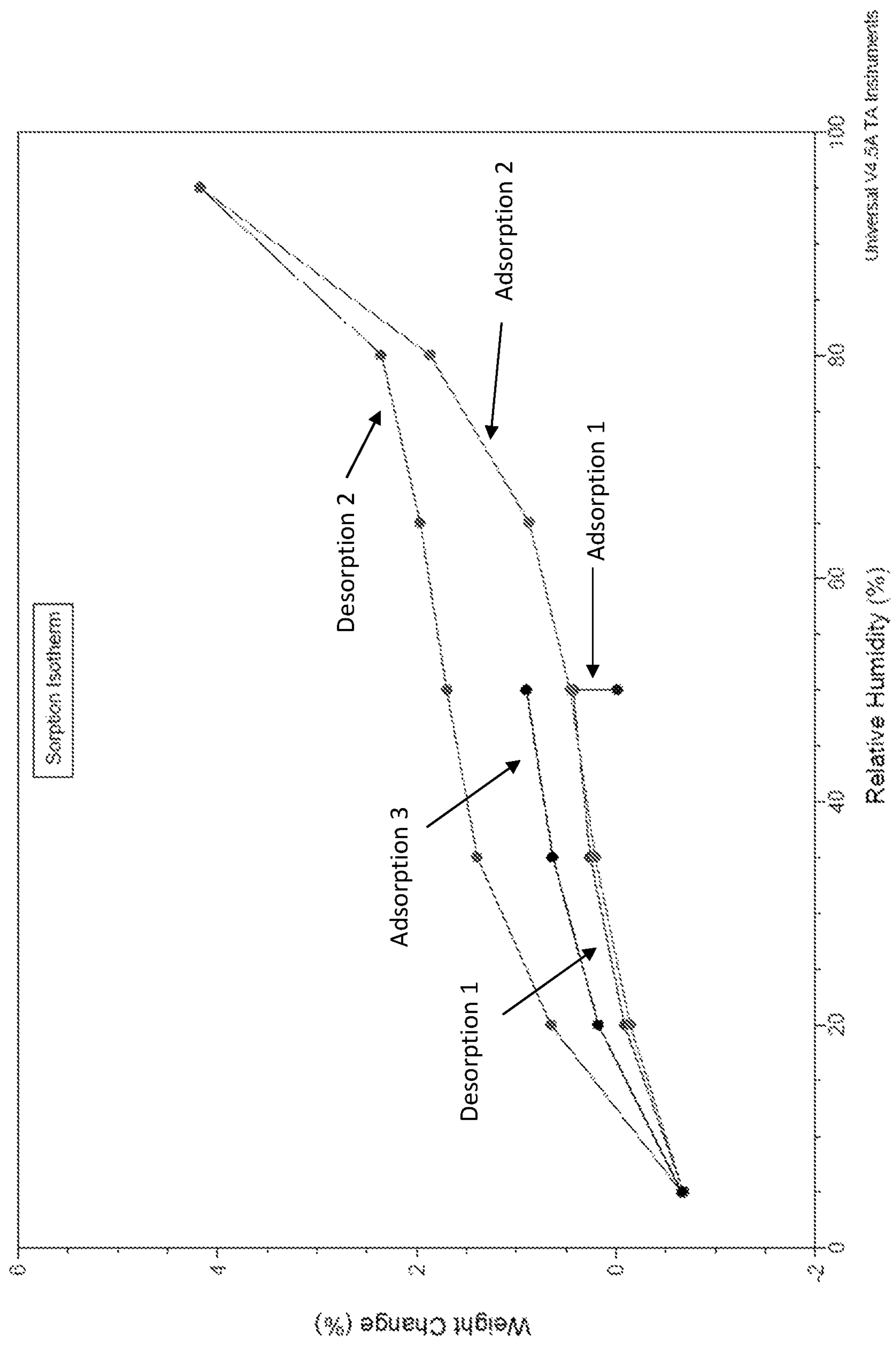
FIG. 5 depicts results of dynamic vapor sorption experiments conducted on crystalline (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt, as further described in Example 4.

In certain embodiments, the compound is further characterized by: weight of the compound increases no more than 10% when placed in an atmosphere that is transitioned from 5% to 95% relative humidity in a dynamic vapor sorption procedure. In certain embodiments, the compound is further characterized by: weight of the compound increases no more than 5% when placed in an atmosphere that is transitioned from 5% to 95% relative humidity in a dynamic vapor sorption procedure. In certain embodiments, the compound has a sorption isotherm substantially the same as shown in FIG. 5.

The description above describes multiple embodiments relating to a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol. The patent application specifically contemplates all combinations of the embodiments.

II. Therapeutic Applications of D-Tartaric Acid Salts of (S)-1-((R)-3-Amino-1-(4-((6-amino-9H-purin-9-yl)methyl)-6-(2,5-difluoro-4-methoxyphenyl)pyridin-3-yl)piperidin-3-yl)-2,2-difluoroethan-1-ol Compounds described herein, such as (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-tartaric acid salt as set forth in Section I, provide therapeutic benefits to subjects suffering from cancer and other diseases or conditions. Accordingly, one aspect of the invention provides a method for treating a disease or condition mediated by nuclear SET domain-containing protein 2 (NSD2). The method comprises administering to a subject in need thereof a therapeutically effective amount of a compound described herein, such as (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-tartaric acid salt, to treat the disease or condition. In certain embodiments, the particular compound is a compound defined by one of the embodiments described above.

Examples of diseases or conditions that are mediated by NSD2 include but is not limited to breast cancer, cervical cancer, skin cancer (particularly skin squamous cell carcinoma), ovarian cancer, gastric cancer, prostate cancer, pancreatic cancer, lung cancer, hepatocellular carcinoma, head and neck cancer, peripheral nerve sheath tumor, osteosarcoma, multiple myeloma, neuroblastoma, leukemia (particularly acute lymphoblastic leukemia), non-Hodgkin's lymphoma (particularly mantle cell lymphoma), and pulmonary arterial hypertension.

In certain embodiments, said disease or condition mediated by NSD2 is cancer.

In certain embodiments, said disease or condition mediated by NSD2 is selected from a solid tumor, leukemia, myeloma, lymphoma, and hypertension. In certain embodiments, said disease or condition mediated by NSD2 is a solid tumor. In certain embodiments, said disease or condition mediated by NSD2 is selected from leukemia, myeloma, and lymphoma. In certain embodiments, said disease or condition mediated by NSD2 is leukemia. In certain embodiments, said disease or condition mediated by NSD2 is myeloma. In certain embodiments, said disease or condition mediated by NSD2 is lymphoma. In certain embodiments, said disease or condition mediated by NSD2 is hypertension.

In certain embodiments, said disease or condition mediated by NSD2 is breast cancer, cervical cancer, skin cancer, ovarian cancer, gastric cancer, prostate cancer, pancreatic cancer, lung cancer, hepatocellular carcinoma, head and neck cancer, peripheral nerve sheath tumor, osteosarcoma, multiple myeloma, neuroblastoma, leukemia, non-Hodgkin's lymphoma, or pulmonary arterial hypertension. In certain embodiments, said disease or condition mediated by NSD2 is breast cancer. In certain embodiments, said disease or condition mediated by NSD2 is cervical cancer. In certain embodiments, said disease or condition mediated by NSD2 is ovarian cancer. In certain embodiments, said disease or condition mediated by NSD2 is gastric cancer. In certain embodiments, said disease or condition mediated by NSD2 is prostate cancer. In certain embodiments, said disease or condition mediated by NSD2 is pancreatic cancer. In certain embodiments, said disease or condition mediated by NSD2 is hepatocellular carcinoma. In certain embodiments, said disease or condition mediated by NSD2 is head and neck cancer. In certain embodiments, said disease or condition mediated by NSD2 is a peripheral nerve sheath tumor. In certain embodiments, said disease or condition mediated by NSD2 is osteosarcoma. In certain embodiments, said disease or condition mediated by NSD2 is multiple myeloma. In certain embodiments, said disease or condition mediated by NSD2 is neuroblastoma. In certain embodiments, said disease or condition mediated by NSD2 is pulmonary arterial hypertension.

In certain embodiments, said disease or condition mediated by NSD2 is acute lymphoblastic leukaemia, skin squamous cell carcinoma, or mantle cell lymphoma. In certain embodiments, said disease or condition mediated by NSD2 is acute lymphoblastic leukaemia. In certain embodiments, said disease or condition mediated by NSD2 is skin squamous cell carcinoma. In certain embodiments, said disease or condition mediated by NSD2 is mantle cell lymphoma.

In certain embodiments, said disease or condition mediated by NSD2 is lung cancer. In certain embodiments, said disease or condition mediated by NSD2 is small cell or non-small cell lung cancer. In certain embodiments, said disease or condition mediated by NSD2 is small cell lung cancer. In certain embodiments, said disease or condition mediated by NSD2 is non-small cell lung cancer.

In certain embodiments, said disease or condition mediated by NSD2 is leukemia. In certain embodiments, said disease or condition mediated by NSD2 is acute lymphoblastic leukemia (ALL), acute myeloid leukemia (AML), chronic myeloid leukemia (CML), or chronic myelomonocytic leukemia (CMML). In certain embodiments, said disease or condition mediated by NSD2 is AML. In certain embodiments, said disease or condition mediated by NSD2 is CML. In certain embodiments, said disease or condition mediated by NSD2 is CMML.

In certain embodiments, said disease or condition mediated by NSD2 is skin cancer. In certain embodiments, said disease or condition mediated by NSD2 is melanoma, basal cell carcinoma, or squamous cell carcinoma. In certain embodiments, said disease or condition mediated by NSD2 is melanoma. In certain embodiments, said disease or condition mediated by NSD2 is basal cell carcinoma.

In certain embodiments, said disease or condition mediated by NSD2 is lymphoma. In certain embodiments, said disease or condition mediated by NSD2 is Hodgkin's lymphoma or non-Hodgkin's lymphoma. In certain embodiments, said disease or condition mediated by NSD2 is Hodgkin's lymphoma. In certain embodiments, said disease or condition mediated by NSD2 is non-Hodgkin's lymphoma. In certain embodiments, said disease or condition mediated by NSD2 is mantle cell lymphoma or diffuse large B cell lymphoma. In certain embodiments, said disease or condition mediated by NSD2 is diffuse large B cell lymphoma.

In certain embodiments, said disease or condition mediated by NSD2 is myeloma.

In certain embodiments, said disease or condition mediated by NSD2 is thyroid cancer. In certain embodiments, said disease or condition mediated by NSD2 is colon cancer.

In certain embodiments, the cancer overexpresses NSD2. In certain embodiments, the cancer has a mutation in NSD2. In certain embodiments, the cancer has an activating mutation in NSD2. In certain embodiments, the cancer has the t(4;14)(p16.3;q32.3) translocation in NSD2. In certain embodiments, the cancer has an E1099K mutation in NSD2. In certain embodiments, the cancer has an T1150A mutation in NSD2.

In certain embodiments, the subject is a human. In certain embodiments, the subject is an adult human. In certain embodiments, the subject is a pediatric human. In certain embodiments, the subject is a geriatric human.

Another aspect of the invention provides for the use of a compound described herein (such as a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol) in the manufacture of a medicament. In certain embodiments, the medicament is for treating a disease or condition described herein, such as cancer.

Another aspect of the invention provides for the use of a compound described herein (such as a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol) for treating a disease or condition, such as a disease or condition described herein (for example, cancer).

Further, compounds described herein, such as a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol) inhibit the activity of nuclear SET domain-containing protein 2 (NSD2). Accordingly, another aspect of the invention provides a method of inhibiting the activity of nuclear SET domain-containing protein 2 (NSD2). The method comprises contacting a NSD2 with an effective amount of a compound described herein, such as a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol, to inhibit the activity of said NSD2. In certain embodiments, the particular compound is a compound defined by one of the embodiments described above.

III. Combination Therapy

Another aspect of the invention provides for combination therapy. Compounds described herein (e.g., a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol) may be used in combination with additional therapeutic agents to treat a disease or condition, such as a cancer.

Accordingly, in some embodiments, the present invention provides a method of treating a disclosed disease or condition comprising administering to a patient in need thereof an effective amount of a compound disclosed herein and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents.

One or more other therapeutic agents may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another.

In certain embodiments, the additional therapeutic agent is an anti-cancer agent, anti-allergic agent, anti-nausea agent (or anti-emetic), pain reliever, cytoprotective agent, or a combination thereof. In certain embodiments, the additional therapeutic agent is an anti-cancer agent, an analgesic, an anti-inflammatory agent, or a combination thereof.

In certain embodiments, the additional therapeutic agent is an anti-cancer agent or chemo-therapeutic agent. Examples of anti-cancer agents considered for use in combination therapies of the invention include but are not limited erlotinib, bortezomib, fulvestrant, sunitib, imatinib mesylate, letrozole, finasunate, platins such as oxaliplatin, carboplatin, and cisplatin, finasunate, fluorouracil, rapamycin, leucovorin, lapatinib, lonafamib, sorafenib, gefitinib, camptothecin, topotecan, bryostatin, adezelesin, anthracyclin, carzelesin, bizelesin, dolastatin, auristatins, duocarmycin, eleutherobin, taxols such as paclitaxel or docetaxel, cyclophosphamide, doxorubicin, vincristine, prednisone or prednisolone, other alkylating agents such as mechlorethamine, chlorambucil, and ifosfamide, antimetabolites such as azathioprine or mercaptopurine, other microtubule inhibitors (vinca alkaloids like vincristine, vinblastine, vinorelbine, and vindesine, as well as taxanes), podophyllotoxins (etoposide, teniposide, etoposide phosphate, and epipodophyllotoxins), topoisomerase inhibitors, other cytotoxins such as actinomycin, daunorubicin, valrubicin, idarubicin, edrecolomab, epirubicin, bleomycin, plicamycin, mitomycin, as well as other anticancer antibodies (cetuximab, bevacizumab, ibritumomab, abagovomab, adecatumumab, afutuzumab, alacizumab, alemtuzumab, anatumomab, apolizumab, bavituximab, belimumab, bivatuzumab mertansine, blinatumomab, brentuximab vedotin, cantuzumab mertansine, catumazomab, cetuximab, citatuzumab bogatox, cixutumumab, clivatuzumab tetraxetan, conatumumab, dacetuzumab, daclizumab, detumomab, ecromeximab, edrecolomab, elotuzumab, epratuzumab, ertumaxomab, etaracizumab, farletuzumab, figitumumab, fresolimumab, galiximab, gembatumumab vedotin, gemtuzumab, ibritumomab tiuxetan, inotuzumab ozogamicin, intetumumab, ipilimumab, iratumumab, labetuzumab, lexatumumab, lintuzumab, lucatumumab, lumilisimab, mapatumumab, matuzumab, milatuzumab, mitumomab, nacolomab tafenatox, naptumomab estafenatox, necitumumab, nimotuzumab, ofatumumab, olaratumab, oportuzumab monatox, oregovomab, panitumumab, pemtumomab, pertuzumab, pintumomab, pritumumab, ramucirumab, rilotumumab, robatumumab, rituximab, sibrotuzumab, tacatuzumab tetraxetan, taplitumomab paptox, tenatumomab, ticilimumab, tigatuzumab, tositumomab or $^{131}$I-tositumomab, trastuzumab, tremelimumab, tuocotuzumab celmoleukin, veltuzumab, visilizumab, volocixumab, votumumab, zalutumumab, zanolimumab, IGN-101, MDX-010, ABX-EGR, EMD72000, ior-t1, MDX-220, MRA, H-11 scFv, huJ591, TriGem, TriAb, R3, MT-201, G-250, ACA-125, Onyvax-105, CD:-960, Cea-Vac, BrevaRex AR54, IMC-1C11, GlioMab-H, ING-1, anti-LCG MAbs, MT-103, KSB-303, Therex, KW2871, anti-HMI.24, Anti-PTHrP, 2C4 antibody, SGN-30, TRAIL-RI MAb, Prostate Cancer antibody, H22xKi-r, ABX-Mai, Imuteran, Monopharm-C), and antibody-drug conjugates comprising any of the above agents (especially auristatins MMAE and MMAF, maytansinoids like DM-1, calicheamycins, or various cytotoxins).

In certain embodiments, the additional therapeutic agent is selected from anastrozole (ARIMIDEX®), bicalutamide (CASODEX®), bleomycin sulfate (BLENOXANE®), busulfan (MYLERAN®), busulfan injection (BUSULFEX®), capecitabine (XELODA®), N4-pentoxycarbonyl-5-deoxy-5-fluorocytidine, carboplatin (PARAPLATIN®), carmustine (BiCNU®), chlorambucil (LEUKERAN®), cisplatin (PLATINOL®), cladribine (LEUSTATIN®), cyclophosphamide (CYTOXAN® or NEOSAR®), cytarabine, cytosine arabinoside (CYTOSAR-U®), cytarabine liposome injection (DEPOCYT®), dacarbazine (DTIC-Dome®), dactinomycin (actinomycin D, COSMEGAN®), daunorubicin hydrochloride (CERUBIDINE®), daunorubicin citrate liposome injection (DAUNOXOME®), dexamethasone, docetaxel (TAXOTERE®), doxorubicin hydrochloride (ADRIAMYCIN®, RUBEX®), etoposide (VEPESID®), fludarabine phosphate (FLUDARA®), 5-fluorouracil (ADRUCIL®, EFUDEX®), flutamide (EULEXIN®), tezacitibine, gemcitabine (difluorodeoxycitidine), hydroxyurea (HYDREA®), idarubicin (IDAMYCIN®), ifosfamide (IFEX®), irinotecan (CAMPTOSAR®), L-asparaginase (ELSPAR®), leucovorin calcium, melphalan (ALKERAN®), 6-mercaptopurine (PURINETHOL®), methotrexate (FOLEX®), mitoxantrone (NOVANTRONE®), gemtuzumab ozogamicin (MYLOTARG™), paclitaxel (TAXOL®), nab-paclitaxel (ABRAXANE®), phoenix (Yttrium90/MX-DTPA), pentostatin, polifeprosan 20 with carmustine implant (GLIADEL®), tamoxifen citrate (NOLVADEX®), teniposide (VUMON®), 6-thioguanine, thiotepa, tirapazamine (TIRAZONE®), topotecan hydrochloride for injection (HYCAMPTIN®), vinblastine (VELBAN®), vincristine (ONCOVIN®), and vinorelbine (NAVELBINE®).

In certain embodiments, the additional therapeutic agent is capable of inhibiting BRAF, MEK, CDK4/6, SHP-2, HDAC, EGFR, MET, mTOR, PI3K or AKT, or a combination thereof. In a particular embodiment, the compounds of the present invention are combined with another therapeutic agent selected from vemurafinib, debrafinib, LGX818, trametinib, MEK162, LEE011, PD-0332991, panobinostat, verinostat, romidepsin, cetuximab, gefitinib, erlotinib, lapatinib, panitumumab, vandetanib, INC280, everolimus, simolimus, BMK120, BYL719 or CLR457, or a combination thereof.

In certain embodiments, the additional therapeutic agent is selected based on the disease or condition that is being treated. For example, in the treatment of melanoma, the additional therapeutic agent is selected from aldesleukin (e.g., PROLEUKIN®), dabrafenib (e.g., TAFINLAR®), dacarbazine, recombinant interferon alfa-2b (e.g., INTRON® A), ipilimumab, trametinib (e.g., MEKINIST®), peginterferon alfa-2b (e.g., PEGINTRON®, SYLATRON™), vemurafenib (e.g., ZELBORAF®)), and ipilimumab (e.g., YERVOY®).

For the treatment of ovarian cancer, the additional therapeutic agent is selected from doxorubicin hydrochloride (Adriamycin®), carboplatin (PARAPLATIN®), cyclophosphamide (CYTOXAN®, NEOSAR®), cisplatin (PLATINOL®, PLATINOL-AQ®), doxorubicin hydrochloride liposome (DOXIL®, DOX-SL®, EVACET®, LIPODOX®), gemcitabine hydrochloride (GEMZAR®), topotecan hydrochloride (HYCAMTIN®), and paclitaxel (TAXOL®).

For the treatment of thyroid cancer, the additional therapeutic agent is selected from doxorubicin hydrochloride (Adriamycin®), cabozantinib-S-malate (COMETRIQ®), and vandetanib (CAPRELSA®).

For the treatment of colon cancer, the additional therapeutic agent is selected from fluorouracil (e.g., ADRUCIL®, EFUDEX®, FLUOROPLEX®), bevacizumab (AVASTIN®), irinotecan hydrochloride (CAMPTOSTAR®), capecitabine (XELODA®), cetuximab (ERBITUX®), oxaliplatin (ELOXATIN®), leucovorin calcium (WELLCOVORIN®), regorafenib (STIVARGA®), panitumumab (VECTIBIX®), and ziv-aflibercept (ZALTRAP®).

For the treatment of lung cancer, the additional therapeutic agent is selected from methotrexate, methotrexate LPF (e.g., FOLEX®, FOLEX PFS®, Abitrexate®, MEXATE®, MEXATE-AQ®), paclitaxel (TAXOL®), paclitaxel albumin-stabilized nanoparticle formulation (ABRAXANE®), afatinib dimaleate (GILOTRIF®), pemetrexed disodium (ALIMTA®), bevacizumab (AVASTIN®), carboplatin (PARAPLATIN®), cisplatin (PLATINOL®, PLATINOL-AQ®), crizotinib (XALKORI®), erlotinib hydrochloride (TARCEVA®), gefitinib (IRESSA®), and gemcitabine hydrochloride (GEMZAR®).

For the treatment of pancreatic cancer, the other therapeutic agent may be selected from fluorouracil (ADRUCIL®), EFUDEX®, FLUOROPLEX®), erlotinib hydrochloride (TARCEVA®), gemcitabine hydrochloride (GEMZAR®), and mitomycin or mitomycin C (MITOZYTREX™, MUTAMYCIN®).

For the treatment of cervical cancer, the additional therapeutic agent is selected from bleomycin (BLENOXANE®), cisplatin (PLATINOL®, PLATINOL-AQ®) and topotecan hydrochloride (HYCAMTIN®).

For the treatment of head and neck cancer, the additional therapeutic agent is selected from methotrexate, methotrexate LPF (e.g., FOLEX®, FOLEX PFS®, Abitrexate®, MEXATE®, MEXATE-AQ®), fluorouracil (ADRUCIL®, EFUDEX®, FLUOROPLEX®), bleomycin (BLENOXANE®), cetuximab (ERBITUX®), cisplatin (PLATINOL®, PLATINOL-AQ®) and docetaxel (TAXOTERE®).

For the treatment of leukemia, including chronic myelomonocytic leukemia (CMML), the additional therapeutic agent is selected from bosutinib (BOSULIF®), cyclophosphamide (CYTOXAN®, NEOSAR®), cytarabine (CYTOSAR-U®, TARABINE PFS®), dasatinib (SPRYCEL®), imatinib mesylate (GLEEVEC®), ponatinib (ICLUSIG®), nilotinib (TASIGNA®) and omacetaxine mepesuccinate (SYNRIBO®).

In some instances, patients may experience allergic reactions to the compounds of the present invention and/or other anti-cancer agent(s) during or after administration. Therefore, anti-allergic agents may be administered to minimize the risk of an allergic reaction. Suitable anti-allergic agents include corticosteroids, such as dexamethasone (e.g., DECADRON®), beclomethasone (e.g., BECLOVENT®), hydrocortisone (also known as cortisone, hydrocortisone sodium succinate, hydrocortisone sodium phosphate; e.g., ALA-CORT®, hydrocortisone phosphate, Solu-CORTEF®, HYDROCORT Acetate® and LANACORT®), prednisolone (e.g., DELTA-Cortel®, ORAPRED®, PEDIAPRED® and PRELONE®), prednisone (e.g., DELTASONE®, LIQUID RED®, METICORTEN® and ORASONE®), methylprednisolone (also known as 6-methylprednisolone, methylprednisolone acetate, methylprednisolone sodium succinate; e.g., DURALONE®, MEDRALONE®, MEDROL®, M-PREDNISOL® and SOLU-MEDROL®); antihistamines, such as diphenhydramine (e.g., BENADRYL®), hydroxyzine, and cyproheptadine; and bronchodilators, such as the beta-adrenergic receptor agonists, albuterol (e.g., PROVENTIL®), and terbutaline (BRETHINE®).

In other instances, patients may experience nausea during and after administration of the compound of the present invention and/or other anti-cancer agent(s). Therefore, anti-emetics may be administered in preventing nausea (upper stomach) and vomiting. Suitable anti-emetics include aprepitant (EMEND®), ondansetron (ZOFRAN®), granisetron HCl (KYTRIL®), lorazepam (ATIVAN®. dexamethasone (DECADRON®), prochlorperazine (COMPAZINE®), casopitant (REZONIC® and Zunrisa®), and combinations thereof.

In yet other instances, medication to alleviate the pain experienced during the treatment period is prescribed to make the patient more comfortable. Common over-the-counter analgesics, such TYLENOL®, are often used. Opioid analgesic drugs such as hydrocodone/paracetamol or hydrocodone/acetaminophen (e.g., VICODIN®), morphine (e.g., ASTRAMORPH® or AVINZA®), oxycodone (e.g., OXYCONTIN® or PERCOCET®), oxymorphone hydrochloride (OPANA®), and fentanyl (e.g., DURAGESIC®) are also useful for moderate or severe pain.

Furthermore, cytoprotective agents (such as neuroprotectants, free-radical scavengers, cardioprotectors, anthracycline extravasation neutralizers, nutrients and the like) may be used as an adjunct therapy to protect normal cells from treatment toxicity and to limit organ toxicities. Suitable cytoprotective agents include amifostine (ETHYOL®), glutamine, dimesna (TAVOCEPT®), mesna (MESNEX®), dexrazoxane (ZINECARD® or TOTECT®), xaliproden (XAPRILA®), and leucovorin (also known as calcium leucovorin, citrovorum factor and folinic acid).

In yet another aspect, a compound of the present invention may be used in combination with known therapeutic processes, for example, with the administration of hormones or in radiation therapy. In certain instances, a compound of the present invention may be used as a radiosensitizer, especially for the treatment of tumors which exhibit poor sensitivity to radiotherapy.

The doses and dosage regimen of the active ingredients used in the combination therapy may be determined by an attending clinician. In certain embodiments, the compound described herein (e.g., a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol) and the additional therapeutic agent(s) are administered in doses commonly employed when such agents are used as monotherapy for treating the disease or condition. In other embodiments, the compound described herein (e.g., a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol) and the additional therapeutic agent(s) are administered in doses lower than the doses commonly employed when such agents are used as monotherapy for treating the disease or condition. In certain embodiments, the compound described herein (e.g., a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol) and the additional therapeutic agent(s) are present in the same composition, which is suitable for oral administration.

In certain embodiments, the compound described herein (e.g., a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of a compound described herein (e.g., a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoro-ethan-1-ol), a pharmaceutically acceptable carrier, vehicle or diluent, and optionally at least one additional therapeutic agent listed above. In certain embodiments, the kit further comprises instructions, such as instructions for treating a disease described herein.

IV. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. In certain embodiments, the invention provides a pharmaceutical composition comprising a compound described herein (e.g., a D-tartaric acid salt of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol) and a pharmaceutically acceptable carrier.

The phrase "therapeutically effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a compound described herein in a therapeutically effective amount for the treatment of a disease or condition described herein.

EXAMPLES

The invention now being generally described, will be more readily understood by reference to the following examples, which are included merely for purposes of illustration of certain aspects and embodiments of the present invention, and are not intended to limit the invention. Starting materials described herein can be obtained from commercial sources or may be readily prepared from commercially available materials using transformations known to those of skill in the art.

Example 1—Preparation of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-Tartaric Acid Salt

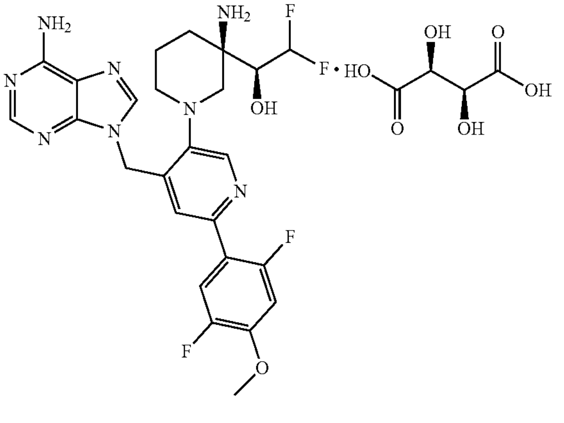

(S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol (1 g) was slurried in acetonitrile (13.5 mL) at ambient temperature. To this slurry, D-tartaric acid (1.1 equivalents) dissolved in water (1.5 mL) was added over approximately one hour. The resulting mixture was warmed to 65° C. and held for two days at this temperature. Then, the resulting slurry was cooled to ambient temperature, filtered, and the collected solid was dried in a vacuum-oven to provide the title compound in 77% yield as a crystalline solid.

Example 2—Preparation of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-Tartaric Acid Salt

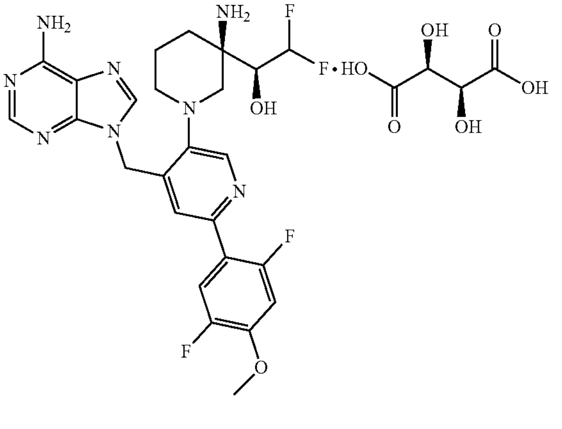

(S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol (1 g) was slurried in ethanol (15 mL) at ambient temperature. To this slurry, D-tartaric acid (1.1 equivalents) dissolved in water (0.75 mL) was added over approximately one hour. The resulting mixture was warmed to 50° C. and held for two days at this temperature. Then, the resulting slurry was cooled to ambient temperature, filtered, and the collected solid was dried in a vacuum-oven to provide the title compound in 79% yield as a crystalline solid.

Example 3—Preparation of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-Tartaric Acid Salt

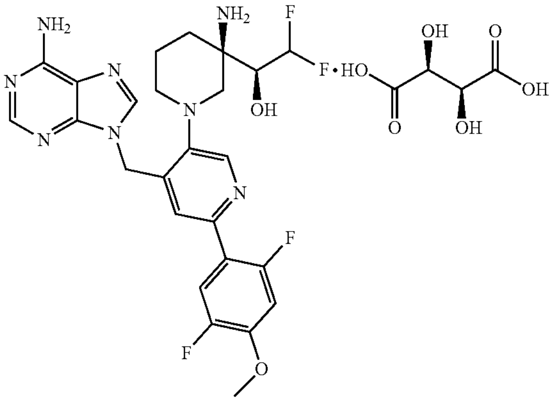

(S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol (1 g) was slurried in isopropyl alcohol (15 mL) at ambient temperature. To this slurry, D-tartaric acid (1.1 equivalents) dissolved in water (0.75 mL) was added over approximately one hour. The resulting mixture was warmed to 50° C. and held for two days at this temperature. Then, the resulting slurry was cooled to ambient temperature, filtered, and the collected solid was dried in a vacuum-oven to provide the title compound in 74% yield as a crystalline solid.

Example 4—Characterization of Crystalline (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-Tartaric Acid Salt

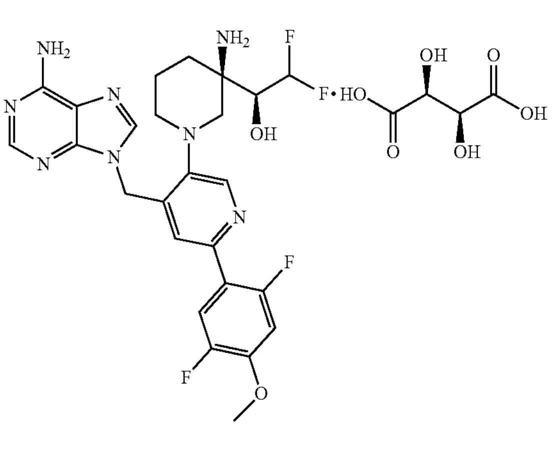

Crystalline (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-tartaric acid salt prepared according to the procedure of Example 1 was analyzed by X-ray powder diffraction, simultaneous thermogravimetric analysis and differential scanning calorimetry, differential scanning calorimetry, dynamic vapor sorption (to analyze hygroscopicity), Karl Fischer titration, and proton nuclear magnetic resonance spectroscopy.

X-ray powder diffraction was performed using either a Rigaku MiniFlex 600 or a Bruker D8 Advance equipped with LYNXEYE detector. Both instruments were operated in reflection mode (i.e. Bragg-Brentano geometry). Samples were prepared on Si zero-return wafers. Parameters for XRPD using the Rigaku MiniFlex 600 were:

| Parameter | Regular Scan | High-Resolution Scan |
|---|---|---|
| X-ray wavelength | Cu Kα1, 1.540598 Å | Cu Kα1, 1.540598 Å |
| X-ray tube setting | 40 kV, 15 mA | 40 kV, 15 mA |
| Slit condition | 1.25° div., Ni kβ filter, 0.3 mm rec. | 1.25° div., Ni kβ filter, 0.3 mm rec. |
| Scan mode | Continuous | Continuous |
| Scan range (°2θ) | 4-30 | 4-40 |
| Step size (°2θ) | 0.05 | 0.05 |
| Scan speed (°/min) | 5 | 1.25 |
| Spin | No | No |

Parameters for XRPD using the Bruker D8 Advance were:

| Parameter | Regular Scan | High-Resolution Scan |
|---|---|---|
| X-ray wavelength | Cu Kα1, 1.540598 Å | Cu Kα1, 1.540598 Å |
| X-ray tube setting | 40 kV, 40 mA | 40 kV, 40 mA |
| Slit condition | 0.6 mm div. + 2.5° soller | 0.6 mm div. + 2.5° soller |
| Scan mode | Step | Step |
| Scan range (°2θ) | 4-30 | 4-40 |
| Step size (°2θ) | 0.03 | 0.02 |
| Dwell time (s/step) | 0.23 | 0.9 |
| Spin | Yes (0.5 Hz) | Yes (0.5 Hz) |

An X-ray powder diffractogram of one batch of the title compound is provided in FIG. 1. Tabulated characteristics of the X-ray powder diffractogram in FIG. 1 are provided in the following table, which lists diffraction angle 2θ, inter-planar distances d, and relative intensity (expressed as a percentage with respect to the most intense peak):

X-Ray Powder Diffractogram Data

| Angle [2θ] | d-spacing [Å] | Relative Intensity [%] |
|---|---|---|
| 6.0 | 14.7 | 40 |
| 8.8 | 10.0 | 36 |
| 10.6 | 8.4 | 53 |
| 10.9 | 8.1 | 44 |
| 13.5 | 6.5 | 15 |
| 15.1 | 5.9 | 31 |
| 15.4 | 5.8 | 18 |
| 15.9 | 5.6 | 100 |
| 16.6 | 5.3 | 6 |
| 17.7 | 5.0 | 35 |
| 17.9 | 5.0 | 16 |
| 18.8 | 4.7 | 16 |
| 19.0 | 4.7 | 26 |
| 20.0 | 4.4 | 22 |
| 20.9 | 4.3 | 57 |
| 21.4 | 4.1 | 30 |
| 21.9 | 4.1 | 18 |
| 22.0 | 4.0 | 21 |
| 22.7 | 3.9 | 29 |
| 22.9 | 3.9 | 12 |
| 23.0 | 3.9 | 22 |

-continued

| Angle [2θ] | d-spacing [Å] | Relative Intensity [%] |
|---|---|---|
| 23.4 | 3.8 | 5 |
| 23.9 | 3.7 | 41 |
| 24.3 | 3.7 | 25 |
| 24.8 | 3.6 | 8 |
| 25.3 | 3.5 | 9 |
| 25.8 | 3.4 | 9 |
| 26.2 | 3.4 | 5 |
| 27.8 | 3.2 | 7 |
| 28.0 | 3.2 | 6 |
| 28.4 | 3.1 | 14 |
| 28.6 | 3.1 | 7 |
| 29.5 | 3.0 | 7 |
| 30.3 | 2.9 | 9 |
| 31.4 | 2.8 | 6 |
| 31.7 | 2.8 | 5 |
| 32.0 | 2.8 | 10 |
| 32.6 | 2.7 | 5 |
| 32.9 | 2.7 | 16 |
| 34.9 | 2.6 | 5 |
| 35.8 | 2.5 | 7 |
| 38.8 | 2.3 | 5. |

An X-ray powder diffractogram of a second batch of the title compound is provided in FIG. 2. Tabulated characteristics of the X-ray powder diffractogram in FIG. 2 are provided in the following table, which lists diffraction angle 2θ, inter-planar distances d, and relative intensity (expressed as a percentage with respect to the most intense peak):

X-Ray Powder Diffractogram Data

| Angle [2θ] | d-spacing [Å] | Relative Intensity [%] |
|---|---|---|
| 6.0 | 14.7 | 72 |
| 8.4 | 10.5 | 6 |
| 8.8 | 10.0 | 32 |
| 10.6 | 8.4 | 58 |
| 10.9 | 8.1 | 88 |
| 12.9 | 6.9 | 6 |
| 13.5 | 6.5 | 24 |
| 14.6 | 6.1 | 6 |
| 15.1 | 5.9 | 31 |
| 15.4 | 5.8 | 24 |
| 15.9 | 5.6 | 100 |
| 16.6 | 5.3 | 5 |
| 17.7 | 5.0 | 28 |
| 17.9 | 5.0 | 26 |
| 18.8 | 4.7 | 22 |
| 19.0 | 4.7 | 36 |
| 20.0 | 4.4 | 40 |
| 20.9 | 4.2 | 82 |
| 21.4 | 4.1 | 37 |
| 21.9 | 4.1 | 29 |
| 22.7 | 3.9 | 35 |
| 23.0 | 3.9 | 35 |
| 23.4 | 3.8 | 10 |
| 24.0 | 3.7 | 49 |
| 24.2 | 3.7 | 29 |
| 24.8 | 3.6 | 10 |
| 25.3 | 3.5 | 13 |
| 25.8 | 3.4 | 9 |
| 26.1 | 3.4 | 7 |
| 27.8 | 3.2 | 7 |
| 28.5 | 3.1 | 8 |
| 29.3 | 3.0 | 6 |
| 29.9 | 3.0 | 9 |
| 30.3 | 2.9 | 9 |
| 31.5 | 2.8 | 5 |
| 32.1 | 2.8 | 9 |

-continued

| Angle [2θ] | d-spacing [Å] | Relative Intensity [%] |
|---|---|---|
| 32.9 | 2.7 | 9 |
| 35.9 | 2.5 | 5 |
| 36.6 | 2.4 | 6. |

Figure 3:
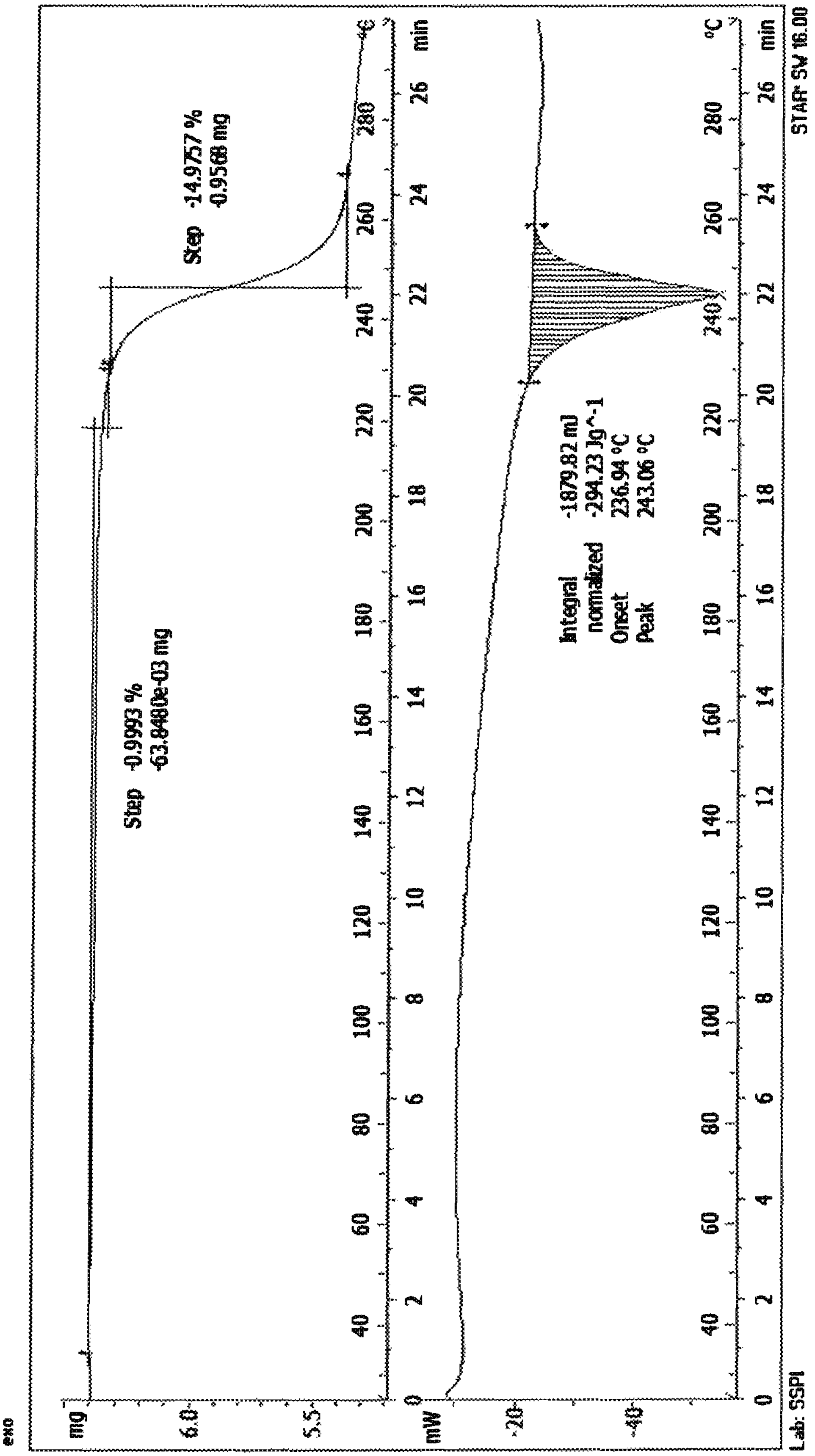
FIG. 3 depicts a thermogravimetric analysis curve and differential scanning calorimetry curve of crystalline (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-tartaric acid salt, as further described in Example 4.

Simultaneous thermogravimetric analysis and differential scanning calorimetry was performed using a Mettler Toledo TGA/DSC$^{3+}$. Protective and purge gas was nitrogen at a flow rate of 20-30 mL/min and 50-100 mL/min, respectively. The sample (5-10 mg) was weighed directly into a hermetic aluminum pan with a pinhole and analyzed according to the following parameters: ramp method, heating rate 10.0° C./min, and temperature range 30 to 300° C. A differential scanning calorimetry curve and thermogravimetric analysis curve of the title compound is provided in FIG. 3.

A separate differential scanning calorimetry analysis was performed using a Mettler Toledo DSC$^{3+}$ (with method gas flow of 60.00 mL/min) or a TA Discovery DSC (with method gas flow of 50.00 mL/min). With either instrument, the sample (1-5 mg) was weighed directly into a 40 μL hermetic aluminum pan with a pinhole and analyzed according to the following parameters: ramp method, heating rate 10.0° C./min, temperature range 30 to 300° C., and method gas $N_2$. A differential scanning calorimetry curve of the title compound obtained according to this procedure is provided in FIG. 4.

The title compound was analyzed for hygroscopicity by dynamic vapor sorption. Dynamic vapor sorption was performed using a Q5000SA. The sample (5-15 mg) was loaded into a metallic quartz sample pan, suspended from a microbalance, and exposed to a humidified stream of nitrogen gas. Weight changes were relative to a matching empty reference pan opposite the sample, suspended from the microbalance. The sample was held for a minimum of 10 min at each humidity level and only progressed to the next humidity level if there was <0.002% change in weight between measurements (interval: 5 s) or 60 min had elapsed. The following program was used:

1. Equilibration at 50% RH
2. 50% to 5% (50%, 35%, 20%, and 5%)
3. 5% to 95%(5%, 20%, 35%, 50%, 65%, 80%, and 95%)
4. 95% to 5% (95%, 80%, 65%, 50%, 35%, 20%, and 5%)
5. 5% to 50%(5%, 20%, 35%, and 50%).

Results of the analysis for hygroscopicity by dynamic vapor sorption are depicted in FIG. 5, where a 4.858% increase in weight was observed when transitioned from 5% to 95% relative humidity.

The title compound was analyzed for water content by Karl Fischer (KF) titration, and determined to have a water content of 1.22 wt %. Karl Fischer (KF) titration for water determination was performed using a Mettler Toledo C20S Coulometric KF Titrator equipped with a current generator cell with a diaphragm, and a double-platinum-pin electrode. The range of detection of the instrument is 1 ppm to 5% water. Aquastar™ CombiCoulomat fritless reagent was used in both the anode and cathode compartments. Samples of approximately 0.03-0.10 g were dissolved in the anode compartment and titrated until the solution potential dropped below 100 mV. Hydranal 1 wt % water standard was used for validation prior to sample analysis.

The title compound was analyzed by proton nuclear magnetic resonance spectroscopy ($^1$H NMR), and determined to have no residual solvent above the limit of detection, and a 1.02:1.00 molar ratio of D-tartaric acid: (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol. Proton nuclear magnetic resonance ($^1$H NMR) spectroscopy was performed on a Bruker Avance 500 MHz spectrometer. Solids were dissolved in 0.60-0.75 mL of deuterated solvent in a 4 mL vial, transferred to an NMR tube (Wilmad 5 mm thin wall 8" 200 MHz, 506-PP-8) and analyzed according to the following parameters:

| Parameter | Value |
|---|---|
| Temperature | 300 K |
| Probe | 5 mm PABBO BB-1H/ D Z-GRD Z113652/0159 |
| Number of Scans | 32 |
| Relaxation Delay | 30.000 s |
| Pulse Width | 14.0000 μs |
| Acquisition Time | 3.2506 s |
| Spectrometer Frequency | 500.13 MHz |

This crystalline form demonstrated water solubility of >2.0 mg/mL at pH 6.8 and 37° C. after both 30 minutes and 24 hours. Additionally, as described in Example 5 below, this crystalline material displayed good stability in an accelerated stability study.

Example 5—Accelerated Stability Study

An accelerated stability study was conducted on the crystalline form of (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt, prepared as described in Example 1. Approximately 12 mg of solid was placed into a 4-mL vial, and then the vial was covered with a Kimwipe. The vial was stored for six days inside a stability chamber producing a relative humidity of 75% at 40° C. Analysis of the recovered salt by HPLC demonstrated good chemical stability: 99.53 area percent purity before the study, and 99.45 area percent purity after the study. Analysis of the recovered salt by XRPD showed no change of the crystalline form.

Example 6—One Year Stability Study

A one-year stability study was conducted on the crystalline form of (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt having an XRDP pattern as set forth in Example 4. In particular, an aliquot of the crystalline (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt was stored for 1 year at a temperature of 25° C.±2° C. where the relative humidity was 60%±5%. A sample of the crystalline (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt was analyzed at the following time points in the experiment: 0 days (i.e., at the start of the experiment), 1 month, 3 months, 6 months, 9 months, and 12 months. The following parameters were evaluated at each time point: physical appearance, water content by coulometric Karl Fischer (CKF) determination, purity by ultra-performance liquid chromatography (UPLC), and total amount of related substances. XRPD analysis was performed on a compound sample at time points 0 days and at 12 months.

Results of the stability study are provided in the table below. The stability study results show that subject crystalline (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt has good stability to storage. For example, the crystalline (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt had low hygroscopicity, as evidenced by very little change in water content during the 12 month stability study. Additionally, the crystalline (S)-1-((R)-3-amino-1-(4-((6-amino-9H-purin-9-yl)methyl)-6-(2,5-difluoro-4-methoxyphenyl) pyridin-3-yl) piperidin-3-yl)-2,2-difluoroethan-1-ol D-tartaric acid salt maintained a high level of purity by UPLC analysis and an XRPD spectrum obtained on a sample of the (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt stored for 12 months matched the XRPD spectrum obtained on said compound at the beginning of the stability study (i.e., day 0).

Results from Stability Study at Temperature of 25° C.±2° C. with Relative Humidity of 60%±5%

| Physical Property Measured | Duration of Storage of Test Compound | | | | | |
|---|---|---|---|---|---|---|
| | Beginning of Experiment (day 0) | 1 month | 3 months | 6 months | 9 months | 12 months |
| Physical Appearance | white wolid | white wolid | white wolid | white wolid | white wolid | white wolid |
| Water Content by CKF (% w/w) | 0.2 | 0.3 | 0.4 | 0.3 | 0.2 | 0.3 |
| API Purity by UPLC (% area in LC trace) | 100.0 | 99.9 | 100.0 | 100.0 | 100.0 | 100.0 |
| Total Amount of Related Substances by UPLC (% w/w) | <0.05 | 0.05 | 0.05 | <0.05 | <0.05 | 0.05 |

Example 7—Six-Month Stability Study at Elevated Temperature & Relative Humidity A six-month stability study was conducted on the crystalline form of (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt having an XRDP pattern as set forth in Example 4. In particular, an aliquot of the crystalline (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt was stored for six months at a temperature of 40° C.±2° C. where the relative humidity was 75%±5%. A sample of the crystalline (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt was analyzed at the following time points in the experiment: 0 days (i.e., at the start of the experiment), 1 month, 3 months, and 6 months. The following parameters were evaluated at each time point: physical appearance, water content by coulometric Karl Fischer (CKF) determination, purity by ultra-performance liquid chromatography (UPLC), and total amount of related substances. XRPD analysis was performed on a compound sample at time points 0 days and at 6 months.

Results of the stability study are provided in the table below. The stability study results show that subject crystalline (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt has good stability to storage. For example, the crystalline (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt had low hygroscopicity, as evidenced by very little change in water content during the 6 month stability study. Additionally, the crystalline (S)-1-((R)-3-amino-1-(4-((6-amino-9H-purin-9-yl)methyl)-6-(2,5-difluoro-4-methoxyphenyl) pyridin-3-yl) piperidin-3-yl)-2,2-difluoroethan-1-ol D-tartaric acid salt maintained a high level of purity by UPLC analysis and an XRPD spectrum obtained on a sample of the (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt stored for 6 months matched the XRPD spectrum obtained on said compound at the beginning of the stability study (i.e., day 0).

Results from Stability Study at Temperature of 40° C.±2° C. with Relative Humidity of 75%±5%

| | Duration of Storage of Test Compound | | | |
|---|---|---|---|---|
| Physical Property Measured | Beginning of Experiment (day 0) | 1 month | 3 months | 6 months |
| Physical Appearance | white wolid | white wolid | white wolid | white wolid |
| Water Content by CKF (% w/w) | 0.2 | 0.4 | 0.4 | 0.4 |
| API Purity by UPLC (% area in LC trace) | 100.0 | 100.0 | 100.0 | 100.0 |
| Total Amount of Related Substances by UPLC (% w/w) | <0.05 | 0.05 | 0.05 | <0.05 |

Example 8—Analysis of Aqueous Solubility

Solubility of test compounds in two different liquids was evaluated: (a) water and (b) fasted state simulated intestinal fluid. Test compounds analyzed were:

crystalline (S)-1-((R)-3-amino-1-(4-((6-amino-9H-purin-9-yl)methyl)-6-(2,5-difluoro-4-methoxyphenyl) pyridin-3-yl)piperidin-3-yl)-2,2-difluoroethan-1-ol D-tartaric acid salt, as set forth in Example 4 (hereinafter "Compound A");

(S)-1-((R)-3-amino-1-(4-((6-amino-9H-purin-9-yl) methyl)-6-(2,5-difluoro-4-methoxyphenyl) pyridin-3-yl)piperidin-3-yl)-2,2-difluoroethan-1-ol fumaric acid salt (hereinafter "Compound B");

(S)-1-((R)-3-amino-1-(4-((6-amino-9H-purin-9-yl) methyl)-6-(2,5-difluoro-4-methoxyphenyl) pyridin-3-yl)piperidin-3-yl)-2,2-difluoroethan-1-ol free base (hereinafter "Compound C").

An aliquot of test compound was placed in the liquid at a temperature of 37° C., and then after 24 hours the concentration of dissolved test compound was determined. pH of the solution at 24 hours was also measured. Results are provided in the following tables.

Test Compound Solubility

| | Test Compound Solubility (mg/mL) | | |
|---|---|---|---|
| Liquid Medium | Compound A | Compound B | Compound C |
| water | 2.4 | 0.488 | 0.0002 |
| fasted state simulated intestinal fluid | 1.6 | 0.506 | 0.298 |

pH Value of the Liquid Medium

| | pH of Liquid Medium at 24 Hours | | |
|---|---|---|---|
| Liquid Medium | Compound A | Compound B | Compound C |
| water | 3.59 | 4.03 | 6.92 |
| fasted state simulated intestinal fluid | 5.71 | 6.06 | 6.61 |

Example 9—Preparation of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-Tartaric Acid Salt

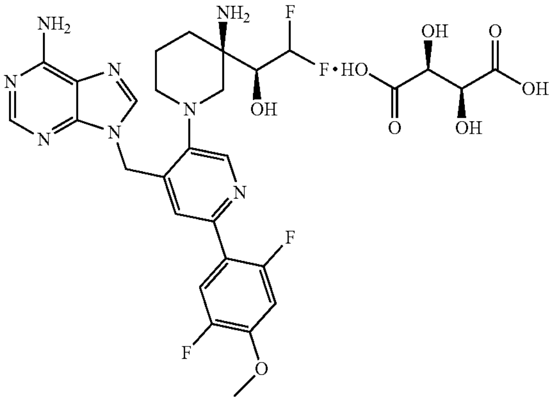

(S)-1-((R)-3-amino-1-(4-((6-amino-9H-purin-9-yl) methyl)-6-(2,5-difluoro-4-methoxyphenyl)pyridin-3-yl)piperidin-3-yl)-2,2-difluoroethan-1-ol (2.28 kg) was dissolved in THF (20.7 kg) in a reactor vessel, and the temperature of the reactor vessel was adjusted to a range of from 30° C. to 40° C., while the reactor vessel was under nitrogen. The resulting mixture was filtered, and ethanol (36.4 kg) was added and the mixture concentrated under reduced pressure. Several times ethanol (18, 18, 19, 19 kg) was added and the mixture concentrated under reduced pressure. The reactor vessel was warmed to a range of from 45° C. to 55° C. D-tartaric acid (0.67 kg) was dissolved in water (2.3 kg) and added slowly to the reactor vessel. The resulting mixture was seeded (20 g) with the desired polymorph (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-tartaric acid salt. The resulting mixture was held at a temperature in the range of 45° C. to 55° C., then cooled to a temperature in the range of 10° C. to 20° C., and then filtered. The resulting solid cake was washed with ethanol/water and dried to provide the title compound (2.77 kg).

Example 10—Preparation of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-Tartaric Acid Salt

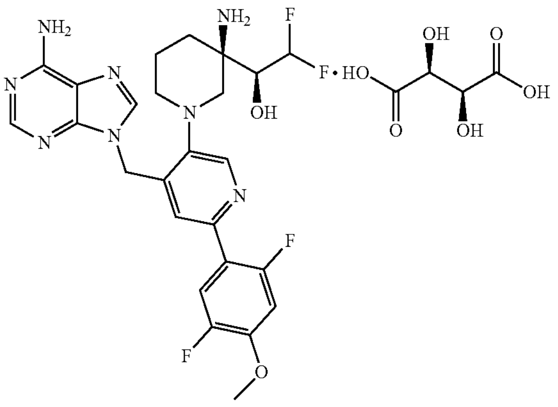

(S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol (15.7 kg) was suspended in ethanol (110 kg) and water was added (23 kg). To the resulting mixture, more ethanol was charged (60 kg) and the temperature of the reactor was adjusted to 60-70° C., and then the reaction mixture was transferred to another reactor vessel with clarification via filtration at 60-70° C. The reactor was washed with ethanol (35 kg) and the resulting mixture was transferred via clarification to the receiving reactor. The reactor was held at a temperature in the range of 60° C. to 70° C. D-tartaric acid (4.7 kg) was mixed with ethanol (11.5 kg), water (1.5 kg), the resulting mixture stirred at 20-30° C., and then dosed into the reactor containing (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol. The resulting mixture was seeded with the desired polymorph of (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol D-tartrate salt (0.17 kg), the D-tartaric/ethanol mixture dosing was completed, and the reactor was cooled to temperature in the range of 50° C. to 60° C. Next, the reactor was further cooled to a temperature in the range of 10° C. to 20° C., and then the mixture was filtered, and the isolated filter cake washed twice with 95% ethanol/water solution (20, 19 kg). The isolated material was then dried to provide the title compound (16.8 kg). $^1H$ NMR (DMSO, 300 MHz) 8.53 (s, 1H), 8.25 (s, 1H), 8.16 (s, 1H), 7.68 (dd, J=12.4, 7.4 Hz, 1H), 7.33 (s, 2H), 7.13 (dd, J=12.9, 7.3 Hz, 7.05 (s, 1H), 6.27 (td, J=54.4, 3.4 Hz, 1H), 5.59 (br s, 2H), 4.01-3.88 (m, 2H), 3.85 (s, 3H), 3.19 (d, J=11.8 Hz, 1H), 3.06-2.88 (m, 3H), 1.92-1.74 (m, 3H). LRMS (ESI+) 547.2 $(M+H^+)$. HRMS (ESI+) 547.2190 $(M+H^+)$.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A compound that is a D-tartaric acid salt of the following compound:

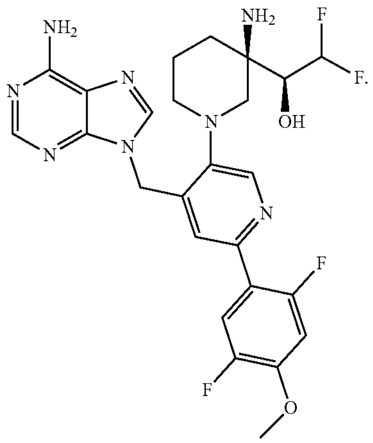 [SMILES: COc1cc(F)c(-c2cc(Cn3cnc4c(N)ncnc43)c(N3CCC[C@](N)([C@H](O)C(F)F)C3)cn2)cc1F]

2. The compound of claim 1, wherein the mole ratio of D-tartaric acid to the following compound is about 1:1:

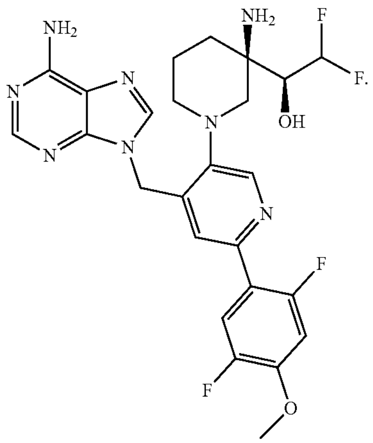 [SMILES: COc1cc(F)c(-c2cc(Cn3cnc4c(N)ncnc43)c(N3CCC[C@](N)([C@H](O)C(F)F)C3)cn2)cc1F]

3. The compound of claim 1, wherein the compound is in crystalline form.

4. The compound of claim 3, wherein the crystalline form exhibits an X-ray powder diffraction pattern comprising peaks at the following diffraction angles (2θ): 6.0±0.2, 8.8±0.2, 10.6±0.2, 10.9±0.2, 15.9±0.2, 20.9±0.2, and 23.9±0.2.

5. The compound of claim 4, wherein the X-ray powder diffraction pattern further comprises a peak at the following diffraction angle (2θ): 15.1±0.2.

6. The compound of claim 5, wherein the X-ray powder diffraction pattern further comprises a peak at the following diffraction angle (2θ): 17.7±0.2.

7. The compound of claim 6, wherein the X-ray powder diffraction pattern further comprises a peak at the following diffraction angle (2θ): 19.0±0.2.

8. The compound of claim 7, wherein the X-ray powder diffraction pattern further comprises a peak at the following diffraction angle (2θ): 21.4±0.2.

9. The compound of claim 8, wherein the X-ray powder diffraction pattern further comprises a peak at the following diffraction angle (2θ): 22.7±0.2.

10. The compound of claim 9, wherein the X-ray powder diffraction pattern further comprises a peak at the following diffraction angle (2θ): 24.3±0.2.

11. The compound of claim 4, wherein the relative intensity of the peak at said diffraction angles (2θ) is at least 25%.

12. The compound of claim 4, wherein the relative intensity of the peak at said diffraction angles (2θ) is at least 15%.

13. The compound of claim 3 characterized by the following X-ray powder diffraction pattern expressed in terms of diffraction angle 2θ, inter-planar distances d, and relative intensity (expressed as a percentage with respect to the most intense peak):

| Angle [2θ] | d-spacing [Å] | Relative Intensity [%] |
|---|---|---|
| 6.0 | 14.7 | 40 |
| 8.8 | 10.0 | 36 |
| 10.6 | 8.4 | 53 |
| 10.9 | 8.1 | 44 |
| 13.5 | 6.5 | 15 |
| 15.1 | 5.9 | 31 |
| 15.4 | 5.8 | 18 |
| 15.9 | 5.6 | 100 |
| 16.6 | 5.3 | 6 |
| 17.7 | 5.0 | 35 |
| 17.9 | 5.0 | 16 |
| 18.8 | 4.7 | 16 |
| 19.0 | 4.7 | 26 |
| 20.0 | 4.4 | 22 |
| 20.9 | 4.3 | 57 |
| 21.4 | 4.1 | 30 |
| 21.9 | 4.1 | 18 |
| 22.0 | 4.0 | 21 |
| 22.7 | 3.9 | 29 |
| 22.9 | 3.9 | 12 |
| 23.0 | 3.9 | 22 |
| 23.4 | 3.8 | 5 |
| 23.9 | 3.7 | 41 |
| 24.3 | 3.7 | 25 |
| 24.8 | 3.6 | 8 |
| 25.3 | 3.5 | 9 |
| 25.8 | 3.4 | 9 |
| 26.2 | 3.4 | 5 |
| 27.8 | 3.2 | 7 |
| 28.0 | 3.2 | 6 |
| 28.4 | 3.1 | 14 |
| 28.6 | 3.1 | 7 |
| 29.5 | 3.0 | 7 |
| 30.3 | 2.9 | 9 |
| 31.4 | 2.8 | 6 |
| 31.7 | 2.8 | 5 |
| 32.0 | 2.8 | 10 |
| 32.6 | 2.7 | 5 |
| 32.9 | 2.7 | 16 |
| 34.9 | 2.6 | 5 |
| 35.8 | 2.5 | 7 |
| 38.8 | 2.3 | 5. |

14. The compound of claim 3, wherein the X-ray powder diffraction pattern is substantially as shown in FIG. 1.

15. The compound of claim 3, wherein the X-ray powder diffraction pattern is substantially as shown in FIG. 2.

16. The compound of claim 4, wherein the compound has a melting point onset as determined by differential scanning calorimetry in the range of from about 225 degrees Celsius to about 240 degrees Celsius.

17. The compound of claim 4, wherein the compound has a melting point onset as determined by differential scanning calorimetry at about 233 degrees Celsius.

18. The compound of claim 4, wherein the compound has a differential scanning calorimetry curve substantially the same as shown in FIG. 4.

19. A pharmaceutical composition comprising a compound of claim 1 and a pharmaceutically acceptable carrier.

20. A method for treating a disease or condition mediated by nuclear SET domain-containing protein 2 (NSD2), comprising administering to a subject in need thereof a therapeutically effective amount of a compound of claim 1 to treat the disease or condition.

21. The method of claim 20, wherein said disease or condition mediated by NSD2 is cancer.

22. The method of claim 20, wherein said disease or condition mediated by NSD2 is selected from a solid tumor, leukemia, myeloma, lymphoma, and hypertension.

23. The method of claim 20, wherein said disease or condition mediated by NSD2 is breast cancer, cervical cancer, skin cancer, ovarian cancer, gastric cancer, prostate cancer, pancreatic cancer, lung cancer, hepatocellular carcinoma, head and neck cancer, peripheral nerve sheath tumor, osteosarcoma, multiple myeloma, neuroblastoma, leukemia, non-Hodgkin's lymphoma, or pulmonary arterial hypertension.

24. The method of claim 20, wherein said disease or condition mediated by NSD2 is acute lymphoblastic leukaemia, skin squamous cell carcinoma, or mantle cell lymphoma.

25. The method of claim 20, wherein the subject is a human.

26. A method of inhibiting the activity of nuclear SET domain-containing protein 2 (NSD2), comprising contacting a NSD2 with an effective amount of a compound of claim 1 to inhibit the activity of said NSD2.

27. A pharmaceutical composition comprising a compound of claim 4 and a pharmaceutically acceptable carrier.

28. A pharmaceutical composition comprising a compound of claim 13 and a pharmaceutically acceptable carrier.

* * * * *